(12) United States Patent
Bedingham et al.

(10) Patent No.: US 7,867,767 B2
(45) Date of Patent: Jan. 11, 2011

(54) VALVE CONTROL SYSTEM FOR A ROTATING MULTIPLEX FLUORESCENCE DETECTION DEVICE

(75) Inventors: William Bedingham, Woodbury, MN (US); Peter D. Ludowise, Cottage Grove, MN (US); Barry W. Robole, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/419,008

(22) Filed: Apr. 6, 2009

(65) Prior Publication Data

US 2009/0189089 A1    Jul. 30, 2009

Related U.S. Application Data

(62) Division of application No. 11/174,957, filed on Jul. 5, 2005, now Pat. No. 7,527,763.

(51) Int. Cl.
*G01N 35/00* (2006.01)
*G01N 21/62* (2006.01)

(52) U.S. Cl. .............................. 436/45; 436/43; 422/63; 422/64; 422/82.05; 435/288.5

(58) Field of Classification Search ........................ None
See application file for complete search history.

(56) References Cited

U.S. PATENT DOCUMENTS

| | | | |
|---|---|---|---|
| 3,918,793 A | 11/1975 | Kraft | 350/91 |
| 3,949,231 A | 4/1976 | Blunck et al. | 250/493 |
| 4,343,991 A | 8/1982 | Fujiwara et al. | 250/227 |
| 4,726,676 A | 2/1988 | Maslaney et al. | |

(Continued)

FOREIGN PATENT DOCUMENTS

CN        1311436 A        9/2001

(Continued)

OTHER PUBLICATIONS

Wenner et al.; "Biosensing on the CD Microfluidic Platform with Genetically Engineered Proteins"; Society of Automotive Engineers, Inc.; Paper 2000-01-2513; pp. 1-6; 2000.

(Continued)

*Primary Examiner*—P. Kathryn Wright
(74) *Attorney, Agent, or Firm*—Nicole J. Einerson

(57) ABSTRACT

Techniques are described for the detection of multiple target species in real-time PCR (polymerase chain reaction). For example, a system comprises a data acquisition device and a detection device coupled to the data acquisition device. The detection device includes a rotating disk having a plurality of process chambers having a plurality of species that emit fluorescent light at different wavelengths. The device further includes a plurality of removable optical modules that are optically configured to excite the species and capture fluorescent light emitted by the species at different wavelengths. A fiber optic bundle coupled to the plurality of removable optical modules conveys the fluorescent light from the optical modules to a single detector. In addition, the device may control the flow of fluid in the disk by locating and selectively opening valves separating chambers by heating the valves with a laser.

18 Claims, 20 Drawing Sheets

U.S. PATENT DOCUMENTS

| | | | |
|---|---|---|---|
| 4,909,990 A | 3/1990 | Block et al. | 422/82.11 |
| 4,927,766 A | 5/1990 | Auerbach et al. | 436/44 |
| 5,296,958 A | 3/1994 | Roddy et al. | |
| 5,414,600 A | 5/1995 | Strobl et al. | 362/32 |
| 5,473,437 A | 12/1995 | Blumenfeld et al. | 356/417 |
| 5,585,069 A | 12/1996 | Zanzucchi et al. | 422/100 |
| 5,639,668 A | 6/1997 | Neel et al. | 436/172 |
| 5,751,874 A | 5/1998 | Chudoba et al. | |
| 5,766,889 A | 6/1998 | Atwood | 435/91.2 |
| 5,928,907 A | 7/1999 | Woudenberg et al. | 435/91.2 |
| 5,994,150 A | 11/1999 | Challener et al. | 436/518 |
| 6,015,674 A | 1/2000 | Woudenberg et al. | 435/6 |
| 6,144,448 A | 11/2000 | Mitoma | 356/317 |
| 6,161,946 A | 12/2000 | Bishop et al. | |
| 6,232,075 B1 | 5/2001 | Williams | |
| 6,339,473 B1 | 1/2002 | Gordon | 356/440 |
| 6,342,349 B1 | 1/2002 | Virtanen | 435/6 |
| 6,442,116 B2 | 8/2002 | Asano | |
| 6,537,211 B1 | 3/2003 | Wang et al. | |
| 6,563,113 B1 | 5/2003 | Amann et al. | |
| 6,563,581 B1 | 5/2003 | Oldham et al. | 356/317 |
| 6,597,450 B1 | 7/2003 | Andrews et al. | 356/317 |
| 6,597,832 B2 | 7/2003 | Cheng | |
| 6,616,304 B2 | 9/2003 | Li | 362/302 |
| 6,627,159 B1 | 9/2003 | Bedingham et al. | 422/100 |
| 6,734,401 B2 | 5/2004 | Bedingham et al. | 219/388 |
| 6,803,999 B1 | 10/2004 | Gordon | 356/73 |
| 6,806,954 B2 | 10/2004 | Sandstrom | 356/317 |
| 6,821,771 B2 | 11/2004 | Festoc | 435/287 |
| 6,833,536 B2 | 12/2004 | Shigeura | 219/553 |
| 6,992,278 B2 | 1/2006 | Sjoberg et al. | 250/231 |
| 6,992,769 B2 | 1/2006 | Gordon | 356/440 |
| 7,088,650 B1 | 8/2006 | Worthington et al. | |
| 7,238,269 B2 | 7/2007 | Gason et al. | 204/459 |
| 7,322,254 B2 | 1/2008 | Bedingham et al. | 73/863 |
| 7,507,575 B2 | 3/2009 | Bedingham et al. | 435/287 |
| 2001/0029036 A1 | 10/2001 | Landers et al. | 435/91.1 |
| 2001/0046712 A1 | 11/2001 | Hang et al. | |
| 2001/0052927 A1 | 12/2001 | Takase et al. | |
| 2002/0039333 A1 | 4/2002 | Tsukahara et al. | |
| 2002/0043626 A1 | 4/2002 | Booker et al. | 250/459 |
| 2002/0047003 A1 | 4/2002 | Bedingham et al. | 219/388 |
| 2002/0048533 A1 | 4/2002 | Harms et al. | 422/99 |
| 2002/0064885 A1 | 5/2002 | Bedingham et al. | 436/174 |
| 2002/0076354 A1 | 6/2002 | Cohen | 422/72 |
| 2002/0104884 A1 | 8/2002 | Meier et al. | |
| 2002/0172980 A1 | 11/2002 | Phan et al. | |
| 2003/0054563 A1 | 3/2003 | Ljungstrom et al. | 436/172 |
| 2003/0077598 A1* | 4/2003 | Phan et al. | 435/6 |
| 2003/0124506 A1 | 7/2003 | Bedingham et al. | 435/4 |
| 2003/0190184 A1 | 10/2003 | O'Brien et al. | |
| 2003/0219754 A1 | 11/2003 | Oleksy et al. | 435/6 |
| 2004/0067051 A1 | 4/2004 | Kylberg et al. | 392/407 |
| 2004/0072335 A1 | 4/2004 | Boege et al. | 435/287 |
| 2004/0126279 A1 | 7/2004 | Renzi et al. | |
| 2004/0224317 A1 | 11/2004 | Kordunsky et al. | 435/6 |
| 2005/0012199 A1 | 1/2005 | Rosenau et al. | |
| 2005/0014249 A1 | 1/2005 | Staimer et al. | 435/287 |
| 2005/0023765 A1 | 2/2005 | Coombs | 277/345 |
| 2005/0032052 A1* | 2/2005 | Pal et al. | 435/6 |
| 2005/0048595 A1 | 3/2005 | Yamatsu et al. | 435/18 |
| 2005/0059062 A1 | 3/2005 | Kaiser | 435/6 |
| 2005/0064582 A1 | 3/2005 | Wittwer et al. | 435/287 |
| 2005/0074784 A1 | 4/2005 | Vo-Dinh | 435/6 |
| 2005/0109396 A1 | 5/2005 | Zucchelli et al. | 137/67 |
| 2005/0130177 A1 | 6/2005 | Bedingham et al. | 435/6 |
| 2005/0151972 A1 | 7/2005 | Boege et al. | 356/417 |
| 2006/0223169 A1 | 10/2006 | Bedingham et al. | 435/287 |
| 2006/0223172 A1 | 10/2006 | Bedingham et al. | 435/288 |
| 2007/0009382 A1 | 1/2007 | Bedingham et al. | 422/63 |
| 2007/0009383 A1 | 1/2007 | Bedingham et al. | 422/63 |
| 2007/0010007 A1 | 1/2007 | Aysta et al. | 435/287 |

FOREIGN PATENT DOCUMENTS

| | | |
|---|---|---|
| CN | 1354361 A | 6/2002 |
| CN | 2522854 Y | 11/2002 |
| CN | 1262833 C | 7/2006 |
| DE | 2 055 944 | 5/1972 |
| GB | 1 599 452 | 10/1981 |
| JP | 61-20839 | 1/1986 |
| WO | WO 91/03915 | 3/1991 |
| WO | WO 98/38510 | 9/1998 |
| WO | WO 01/01112 | 1/2001 |
| WO | WO 01/65242 | 9/2001 |
| WO | WO 02/073605 | 9/2002 |
| WO | WO 03/058253 | 7/2003 |
| WO | WO 03/098278 | 11/2003 |
| WO | WO 03/098279 | 11/2003 |
| WO | WO 03/102226 | 12/2003 |
| WO | WO 2004/079343 | 9/2004 |
| WO | WO 2004/087950 | 10/2004 |
| WO | WO 2005/030395 * | 4/2005 |

OTHER PUBLICATIONS

Lee et al.; "A novel real-time PCR machine with a miniature spectrometer for fluorescence sensing in a micro liter volume glass capillary"; Sensors and Actuators B 100 (2004) 401-410.

Lee et al.; "Development of a CCD-based fluorimeter for real-time PCR machine"; Sensors and Actuators B 107 (2005) 872-881.

* cited by examiner

VALVE CONTROL SYSTEM FOR A ROTATING MULTIPLEX FLUORESCENCE DETECTION DEVICE

CROSS REFERENCE TO RELATED APPLICATIONS

This application is a division of U.S. patent application Ser. No. 11/174,957, filed Jul. 5, 2005, now U.S. Pat. No. 7,527,763, which is incorporated herein by reference.

TECHNICAL FIELD

The invention relates to assaying systems and, more particularly, techniques for controlling fluid flow during the detection of multiple target species using fluorescent dyes.

BACKGROUND

Optical disc systems are often used to perform various biological, chemical or bio-chemical assays. In a typical system, a rotatable disc is used as a medium for storing and processing fluid specimens, such as blood, plasma, serum, urine or other fluid. In some cases, the fluids within the disk may need to be moved from one location to another during the processing.

One type of analysis is polymerase chain reaction (PCR), which is often used for nucleic acid sequence analysis. In particular, PCR is often used for DNA sequencing, cloning, genetic mapping, and other forms of nucleic acid sequence analysis.

In general, PCR relies on the ability of DNA-copying enzymes to remain stable at high temperatures. There are three major steps in PCR: denaturation, annealing, and extension. During the denaturation, a liquid sample is heated at approximately 94° C. During this process, double DNA strands "melt" open into single stranded DNA and all enzymatic reactions stop. During annealing, the single stranded DNA is cooled to 54° C. At this temperature, primers bind or "anneal" to the ends of the DNA strands. During extension, the sample is heated to 75° C. At this temperature, nucleotides add to the primers and eventually a complementary copy of the DNA template is formed.

There are a number of existing PCR instruments designed to determine levels of specific DNA and RNA sequences in the sample during the PCR in real-time. Many of the instruments are based on the use of fluorescent dyes. In particular, many conventional real-time PCR instruments detect a fluorescent signal produced proportionally during amplification of a PCR product.

Conventional real-time PCR instruments use different methods for detection of different fluorescent dyes. For example, some conventional PCR instruments incorporate white light sources with filter wheels for spectrally resolving each dye. The white light sources are tungsten halogen bulbs, which have a lifetime maxima of a few thousand hours. The filter wheels are typically complicated electromechanical parts that are susceptible to wear.

SUMMARY

In general, the invention relates to techniques for the detection of multiple target species in real-time PCR (polymerase chain reaction), referred to herein as multiplex PCR. In particular, a multiplex fluorescence detection device is described that incorporates a plurality of optical modules. Each of the optical modules may be optimized for detection of a respective fluorescent dye at a discrete wavelength band. In other words, the optical modules may be used to interrogate multiple, parallel reactions at different wavelengths. The reaction may, for example, occur within a single process chamber (e.g., well) of a rotating disk. Additionally, each optical module may be removable to quickly change the detection capabilities of the device.

The plurality of optical modules may be optically coupled to a single detector by a multi-legged optical fiber bundle. In this manner, multiplexing can be achieved by using a plurality of optical modules and a single detector, e.g., a photomultiplier tube. The optical components in each optical module may be selected to maximize sensitivity and minimize the amount of spectral crosstalk, i.e., signals from one dye on another optical module.

The device also includes a laser valve control system for mapping and opening valves on the disk. The laser control valve control system may have two power settings. In a low power setting, the system emits a laser beam that is detected by sensor through a slot in the disk to map the disk position with respect to the rotating platform rotating the disk. The map may then be used to locate selected valves separating two or more chambers on the disk. Once located, the laser control valve system may focus higher-energy laser light on a valve to open the valve and allow contents to flow from a holding chamber to a process chamber while the disk is rotated.

In one embodiment, a device comprises a motor to rotate a disk having a holding chamber separated from a process chamber by a channel having a valve and an energy source that outputs electromagnetic energy at a first level to determine a position of the disk and at a second level to open the valve to permit fluid to flow from the holding chamber to the process chamber.

In another embodiment, a system comprises a data acquisition device. The system further comprises a detection device coupled to the data acquisition device, wherein the detection device comprises a motor to rotate a disk having a holding chamber separated from a process chamber by a channel having a valve; an energy source that outputs electromagnetic energy to determine a position of the disk and open the valve to permit fluid to flow from the holding chamber to the process chamber; and a sensor that outputs a signal upon detection of the electromagnetic energy.

In an additional embodiment, a method comprises rotating a disk having a holding chamber separated from a process chamber by a channel having a valve; emitting electromagnetic energy at a first level to determine a position of the disk; and emitting electromagnetic energy at a second level to open the valve to permit fluid to flow from the holding chamber to the process chamber.

The invention may provide one or more advantages. For example, the laser valve control system may be used to locate the exact position of the disk and create a map of the disk position. Moreover, the system may then use the map to position the laser over the valves on the disk to open them as needed. This self-calibrating technique may decrease operating time and increase laser accuracy.

While the device may be capable of conducting real-time PCR, the device may be capable of analyzing any type of biological reaction while it occurs. The device may be able to modulate the temperature of each reaction independently or as a selected group, and the device may be able to support multiple stages of reactions by including a valve between two or more chambers.

In some embodiments, the device may be portable and robust to allow operation in remote areas or temporary laboratories. The device may include a data acquisition computer for analyzing the reactions in real-time, or the device may communicate the data to another device through wired or wireless communication interfaces.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
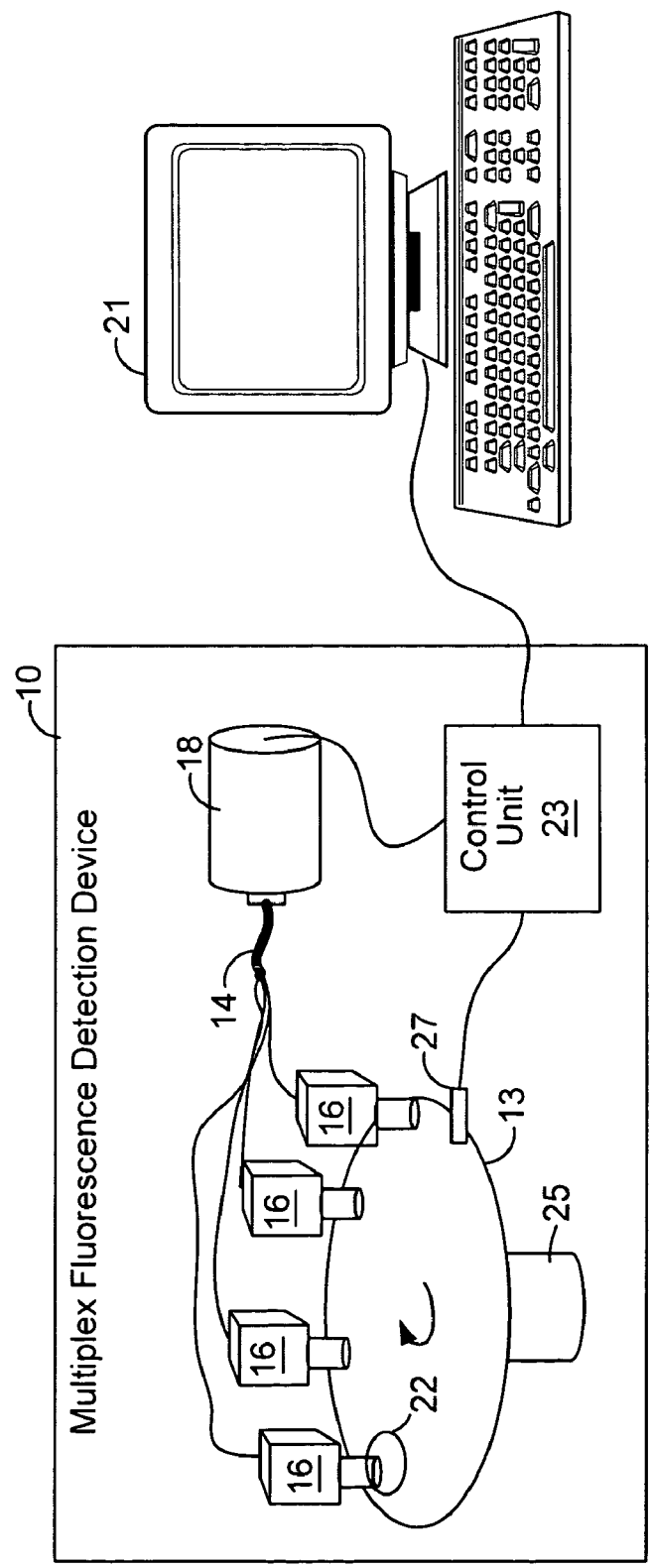
FIG. 1 is a block diagram illustrating an exemplary embodiment of a multiplex fluorescence detection device.

FIG. 1 is a block diagram illustrating an exemplary embodiment of a multiplex fluorescence detection device 10. In the illustrated example, device 10 has four optical modules 16 that provide four "channels" for optical detection of four different dyes. In particular, device 10 has four optical modules 16 that excite different regions of rotating disk 13 at any given time, and collect emitted fluorescent light energy at different wavelengths from the dyes. As a result, modules 16 may be used to interrogate multiple, parallel reactions occurring within sample 22.

The multiple reactions may, for example, occur simultaneously within a single chamber of a rotating disk 13. Each of optical modules 16 interrogates sample 22 and collects fluorescent light energy at different wavelengths as the disk 13 rotates. For example, excitation sources within modules 16 may be sequentially activated for periods sufficient to collect data at the corresponding wavelengths. That is, an optical module 16A may be activated for a period of time to collect data at a first range of wavelengths selected for a first dye corresponding to a first reaction. The excitation source may then be deactivated, and an excitation source within module 16B may be activated to interrogate sample 22 at a second range of wavelengths selected for a second dye corresponding to a second reaction. This process continues until data has been captured from all optical modules 16. In one embodiment, each of the excitation sources within optical modules 16 is activated for an initial period of approximately two seconds to reach steady state followed by an interrogation period which lasts for 10-50 rotations of disk 13. In other embodiments, the excitation sources may be sequenced for shorter (e.g., 1 or 2 milliseconds) or longer periods. In some embodiments, more than one optical module may be activated simultaneously for concurrent interrogation of sample 22 without stopping the rotation of disk 13.

Although a single sample 22 is illustrated, disk 13 may contain a plurality of chambers holding samples. Optical modules 16 may interrogate some or all of the different chambers at different wavelengths. In one embodiment, disk 13 includes 96 chambers space around a circumference of disk 13. With a 96 chamber disk and four optical modules 16, device 10 may be capable of acquiring data from 384 different species.

In one embodiment, optical modules 16 include excitation sources that are inexpensive high power light emitting diodes (LEDs), which are commercially available in a variety of wavelengths and have long lifetimes (e.g., 100,000 hours or more). In another embodiment, conventional halogen bulbs or mercury lamps may be used as excitation sources.

As illustrated in FIG. 1, each of optical modules 16 may be coupled to one leg of a fiber optic bundle 14. Fiber optic bundle 14 provides a flexible mechanism for collection of fluorescent signals from optical modules 16 without loss of sensitivity. In general, a fiber optic bundle comprises multiple optical fibers laid side by side and bonded together at the ends and encased in a flexible protective jacket. Alternatively, fiber optic bundle 14 may comprise a smaller number of discrete, large diameter multi-mode fibers, either glass or plastic, having a common end. For example, for a four-optical module device, fiber optic bundle 16 may comprise four discrete multimode fibers, each having a 1 mm core diameter. The common end of the bundle contains the four fibers bound together. In this example, the aperture of detector 18 may be 8 mm, which is more than sufficient for coupling to the four fibers.

In this example, fiber optic bundle 14 couples optical modules 16 to a single detector 18. The optical fibers carry the fluorescent light collected by optical modules 16 and effectively deliver the captured light to detector 18. In one embodiment, detector 18 is a photomultiplier tube. In another embodiment, the detector may include multiple photomultiplier elements, one for each optical fiber, within the single detector. In other embodiments, one or more solid-state detectors may be used.

The use of a single detector 18 may be advantageous in that it allows use of a highly sensitive and possibly expensive detector (e.g., a photomultiplier), while maintaining a minimal cost in that only a single detector need be used. A single detector is discussed herein; however, one or more detectors may be included for detecting a greater number of dyes. For example, four additional optical modules 16 and a second detector may be added to the system to allow for the detection of eight different wavelengths emitted from one disk. An exemplary fiber optic bundle coupled to a single detector for use with rotating disk 13 is described in U.S. Patent Application Publication No. 2006-0223172 entitled "MULTIPLEX FLUORESCENCE DETECTION DEVICE HAVING FIBER BUNDLE COUPLING MULTIPLE OPTICAL MODULES TO A COMMON DETECTOR," filed on Jul. 5, 2005, the entire content of which is hereby incorporated by reference.

Optical modules 16 are removable from the device and easily interchangeable with other optical modules that are optimized for interrogation at different wavelengths. For example, optical modules 16 may be physically mounted within locations of a module housing. Each of optical modules 16 may be easily inserted within a respective location of the housing along guides (e.g., recessed grooves) that mate with one or more marking (e.g., guide pins) of the optical module. Each of optical modules 16 may be secured within the carriage by a latch, magnet, screw or other fastening device. Each optical module includes an optical output port (shown in FIGS. 6 and 7) for coupling to one leg of fiber optic bundle 14. The optical output port may have a threaded end coupled to a threaded connector of the leg. Alternatively, a form of "quick-connect" may be used (e.g., a slidable connection having an o-ring and a catch pin) that allows fiber optic bundle 14 to be slidably engaged and disengaged from the optical output port. Moreover, each of optical modules 16 may have one or more electrical contacts pads or flex circuits for electronically coupling to control unit 23 when fully inserted. Exemplary removable optical modules for use with rotating disk 13 is described in U.S. Pat. No. 7,507,575 entitled "MULTIPLEX FLUORESCENCE DETECTION DEVICE HAVING REMOVABLE OPTICAL MODULES," filed on Jul. 5, 2005, the entire content of which is hereby incorporated by reference.

The modular architecture of device 10 allows the device to be easily adapted for all of the fluorescent dyes used in a given analysis environment, such as multiplex PCR. Other chemistries that may be used in device 10 include Invader (Third Wave, Madison, Wis.), Transcripted-mediated Amplification (GenProbe, San Diego, Calif.), fluorescence labeled enzyme linked immunosorbent assay (ELISA) or fluorescence in situ hybridization (FISH). The modular architecture of device 10 may provide another advantage in that the sensitivity of each optical module 16 can be optimized by choice of the corresponding excitation source (not shown) and excitation and detection filters for a small specific target range of wavelengths in order to selectively excite and detect a corresponding dye in the multiplex reaction.

For purpose of example, device 10 is illustrated in a 4-color multiplex arrangement, but more or less channels can be used with the appropriate fiber optic bundle 14. This modular design allows a user to easily upgrade device 10 in the field by simply adding another optical module 16 to base 20 and inserting one leg of fiber optic bundle 14 into the new optical module. Optical modules 16 may have integrated electronics that identify the optical modules and download calibration data into an internal control module or other internal electronics (e.g., control unit 23) of device 10.

In the example of FIG. 1, samples 22 are contained in chambers of disk 13, which is mounted on a rotating platform under the control of control unit 23. A slot sensor trigger 27 provides an output signal utilized by control unit 23 for synchronizing data acquisition device 21 with chamber position during disk rotation. Slot sensor trigger 27 may be a mechanical, electrical, magnetic, or optical sensor. For example, as described in further detail below, slot sensor trigger 27 may include a light source that emits a beam of light to through a slot formed through disk 13 that is detected each revolution of the disk. As another example, slot sensor trigger may sense reflected light for purposes of synchronizing the rotation of disk 13 and data acquisition by modules 16 and detector 18. In other embodiments, disk 13 may include a tab, protrusion or reflective surface in addition to or in place of the slot. Slot sensor trigger 27 may use any physical structure or mechanism to locate the radial position of disk 13 as it rotates. Optical modules 16 may be physically mounted above rotating platform 25. As a result, optical modules 16 are overlapped with different chambers at any one time.

Detection device 10 also includes a heating element (not shown) for modulating the temperature of the sample 22 on disk 13. The heating element may comprise a cylindrical halogen bulb contained within a reflective enclosure. The reflective chamber is shaped to focus radiation from the bulb onto a radial section of disk 13. Generally, the heated area of disk 13 would comprise an annular ring as disk 13 spins. In this embodiment, the shape of the reflective enclosure may be a combination of elliptical and spherical geometries that allow precise focusing. In other embodiments, the reflective enclosure may be of a different shape or the bulb may broadly irradiate a larger area. In other embodiments, the reflective enclosure may be shaped to focus the radiation from the bulb onto a single area of the disk 13, such as a single process chamber containing a sample 22.

In some embodiments, the heating element may heat air and force the hot air over one or more samples to modulate the temperature. Additionally, the samples may be heated directly by the disk. In this case, the heating element may be located in platform 25 and thermally couple to disk 13. Electrical resistance within the heating element may heat a selected region of the disk as controlled by control unit 23. For example, a region may contain one or more chambers, possibly the entire disk. An exemplary heating element for use with rotating disk 13 is described in U.S. Patent Application Publication No. 2007-0009382, entitled "HEATING ELEMENT FOR A ROTATING MULTIPLEX FLUORESCENCE DETECTION DEVICE," filed on Jul. 5, 2005, the entire content of which is hereby incorporated by reference.

Alternatively, or in addition, device 10 may also includes a cooling component (not shown). A fan is included in device 10 to supply cold air, i.e., room temperature air, to disk 13. Cooling may be needed to modulate the temperature of the sample appropriately and store samples after an experiment has completed. In other embodiments, the cooling component may include thermal coupling between platform 25 and disk 13, as platform 25 may reduce its temperature when needed.

For example, some biological samples may be stored at 4 degrees Celsius to reduce enzyme activity or protein denaturing.

Detection device 10 may also be capable of controlling reaction species contained within a process chamber. For example, it may be beneficial to load some species in a process chamber to generate one reaction and later add another species to the sample once the first reaction has terminated. A valve control system may be utilized to control a valve separating an inner holding chamber from the process chamber, thereby controlling the addition of species to the chamber during rotation of disk 13. The valve control system may be located within or mounted to one of optical modules 16 or separate from the optical modules. Directly below the laser, under disk 13, may be a laser sensor for positioning the laser relative to disk 13.

In one embodiment, the valve control system includes a near infrared (NIR) laser capable of being driven at two or more power levels in combination with a sensor. Under a low power setting, the laser may be used for positioning disk 13 and targeting select valves, e.g., by the sensor sensing the NIR light emitted by the laser though a slot in disk 13. Once the targeted valve is rotated into position, control unit 23 directs the laser to output a short burst of high power energy to heat the valve and open the targeted valve. The burst of energy forms a void in the valve, e.g., by piercing, melting or ablating, causing the valve to open and allowing a fluid to flow through a channel from an inner holding chamber to an outside process chamber. In some embodiments, disk 13 may contain a plurality of valves of various sizes and materials to generate a plurality of reactions in sequence. More than one set of valve control system may be used when utilizing a disk having multiple chamber valves.

Data acquisition device 21 may collect data from device 10 for each dye either sequentially or in parallel. In one embodiment, data acquisition system 21 collects the data from optical modules 16 in sequence, and corrects the spatial overlap by a trigger delay for each one of the optical modules measured from the output signal received from slot sensor trigger 27.

One application for device 10 is real-time PCR, but the techniques described herein may be extended to other platforms that utilize fluorescence detection at multiple wavelengths. Device 10 may combine rapid thermal cycling, utilizing the heating element, and centrifugally driven microfluidics for isolation, amplification, and detection of nucleic acids. By making use of multiplex fluorescence detection, multiple target species may be detected and analyzed in parallel.

For real-time PCR, fluorescence is used to measure the amount of amplification in one of three general techniques. The first technique is the use of a dye, such as Sybr Green (Molecular Probes, Eugene, Oreg.), whose fluorescence increases upon binding to double-stranded DNA. The second technique uses fluorescently labeled probes whose fluorescence changes when bound to the amplified target sequence (hybridization probes, hairpin probes, etc.). This technique is similar to using a double-stranded DNA binding dye, but is more specific because the probe will bind only to a certain section of the target sequence. The third technique is the use of hydrolysis probes (Taqman™, Applied BioSystems, Foster City Calif.), in which the exonuclease activity of the polymerase enzyme cleaves a quencher molecule from the probe during the extension phase of PCR, making it fluorescently active.

In each of the approaches, fluorescence is linearly proportional to the amplified target concentration. Data acquisition system 21 measures an output signal from detector 18 (or alternatively optionally sampled and communicated by control unit 23) during the PCR reaction to observe the amplification in near real-time. In multiplex PCR, the multiple targets are labeled with different dyes that are measured independently. Generally speaking, each dye will have different absorbance and emission spectra. For this reason, optical modules 16 may have excitation sources, lenses and related filters that are optically selected for interrogation of sample 22 at different wavelengths.

Some examples of suitable construction techniques or materials that may be adapted for use in connection with the present invention may be described in, e.g., commonly-assigned U.S. Pat. No. 6,734,401 titled "ENHANCED SAMPLE PROCESSING DEVICES SYSTEMS AND METHODS" (Bedingham et al.) and U.S. Pat. No. 7,026,168 titled "SAMPLE PROCESSING DEVICES." Other useable device constructions may be found in, e.g., U.S. Provisional Patent Application Ser. No. 60/214,508 filed on Jun. 28, 2000 and entitled "THERMAL PROCESSING DEVICES AND METHODS"; U.S. Provisional Patent Application Ser. No. 60/214,642 filed on Jun. 28, 2000 and entitled "SAMPLE PROCESSING DEVICES, SYSTEMS AND METHODS"; U.S. Provisional Patent Application Ser. No. 60/237,072 filed on Oct. 2, 2000 and entitled "SAMPLE PROCESSING DEVICES, SYSTEMS AND METHODS"; U.S. Provisional Patent Application Ser. No. 60/260,063 filed on Jan. 6, 2001 and titled "SAMPLE PROCESSING DEVICES, SYSTEMS AND METHODS"; U.S. Provisional Patent Application Ser. No. 60/284,637 filed on Apr. 18, 2001 and titled "ENHANCED SAMPLE PROCESSING DEVICES, SYSTEMS AND METHODS"; and U.S. Pat. No. 6,814,935 titled "SAMPLE PROCESSING DEVICES AND CARRIERS." Other potential device constructions may be found in, e.g., U.S. Pat. No. 6,627,159 titled "CENTRIFUGAL FILLING OF SAMPLE PROCESSING DEVICES" (Bedingham et al.). The entire content of these disclosures are incorporated herein by reference.

Figure 2:
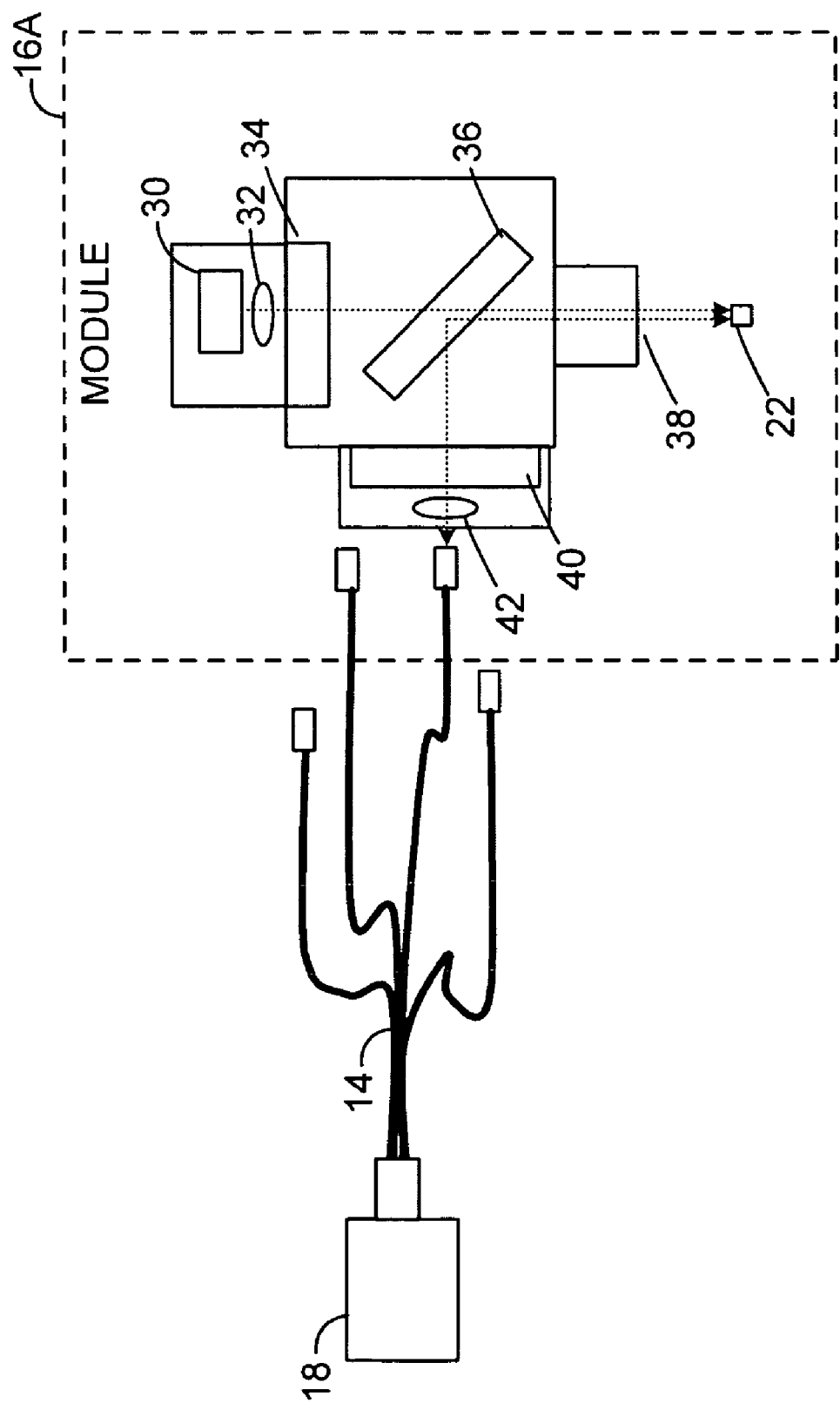
FIG. 2 is a schematic diagram illustrating an exemplary detection module, which may correspond to any of a plurality of detection modules of the fluorescence detection device of FIG. 1.

FIG. 2 is a schematic diagram illustrating an exemplary optical module 16A, which may correspond to any of optical modules 16 of FIG. 1. In this example, optical module 16A contains a high-power excitation source, LED 30, a collimating lens 32, an excitation filter 34, a dichroic filter 36, a focusing lens 38, a detection filter 40, and a lens 42 to focus the fluorescence into one leg of fiber optic bundle 14.

Consequently, the excitation light from LED 30 is collimated by collimating lens 32, filtered by excitation filter 34, transmitted through dichroic filter 36, and focused into the sample 22 by focusing lens 38. The resulting fluorescence emitted by the sample is collected by the same focusing lens 38, reflected off of dichroic filter 36, and filtered by detection filter 40 before being focused into one leg of fiber optic bundle 14. The optic bundle 14 then transfers the light to detector 18.

LED 30, collimating lens 32, excitation filter 34, dichroic filter 36, focusing lens 38, detection filter 40, and lens 42 are selected based on the specific absorption and emission bands of the multiplex dye with which optical module 16A is to be used. In this manner, multiple optical modules 16 may be configured and loaded within device 10 to target different dyes.

Table 1 lists exemplary components that may be used in a 4-channel multiplex fluorescence detection device 10 for a variety of fluorescent dyes. FAM, HEX, JOE, VIC, TET, ROX are trademarks of Applera, Norwalk, Calif. Tamra is a trademark of AnaSpec, San Jose, Calif. Texas Red is a trademark of Molecular Probes. Cy 5 is a trademark of Amersham, Buckinghamshire, United Kingdom.

TABLE 1

| Optical Module | LED | Excitation Filter | Detection Filter | Dye |
|---|---|---|---|---|
| 1 | blue | 475 nm | 520 nm | FAM, Sybr Green |
| 2 | green | 530 nm | 555 nm | HEX, JOE, VIC, TET |
| 3 | orange | 580 nm | 610 nm | TAMRA, ROX, Texas Red |
| 4 | red | 630 nm | 670 nm | Cy 5 |

One advantage of the described modular, multiplex detection architecture is the flexibility in optimizing detection for a wide variety of dyes. Conceivably a user may have a bank of several different optical modules that can be plugged into device 10 as needed, of which N can used at any one time, where N is the maximum number of channels supported by the device. Therefore, device 10 and optical modules 16 may be used with any fluorescent dye and PCR detection method. A larger fiber optic bundle may be used to support a larger number of detection channels. Moreover, multiple fiber optic bundles may be used with multiple detectors. For example, two 4-legged fiber optic bundles may be used with eight optical modules 16 and two detectors 18.

Figure 3:
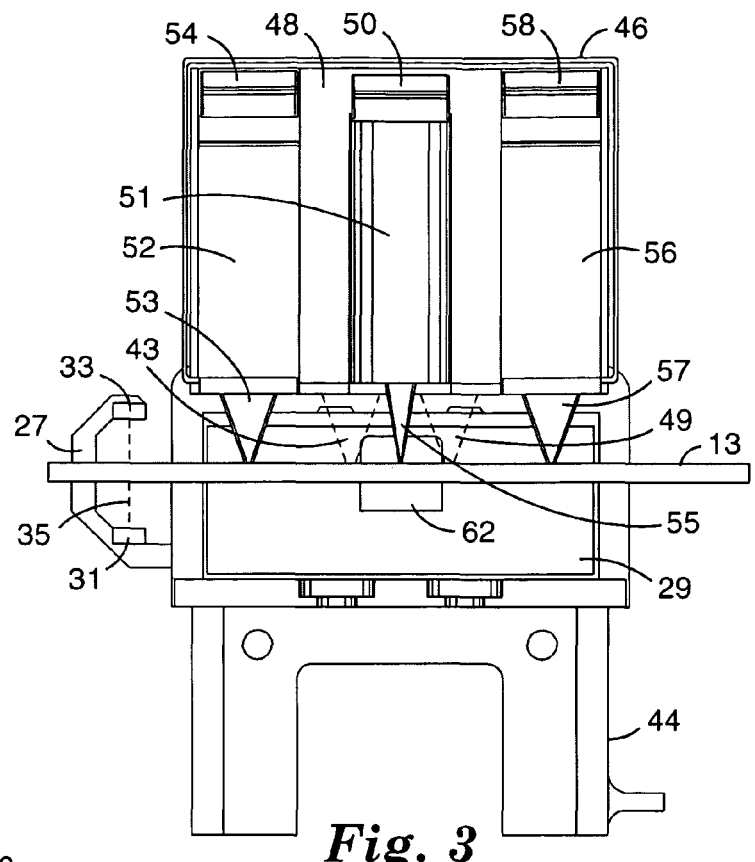
FIG. 3 is a perspective diagram illustrating a front view of an exemplary set of removable optical modules within the device housing.

FIG. 3 is a perspective diagram illustrating a front view of an exemplary set of removable optical modules within the device housing. In the example of FIG. 3, device 10 includes base arm 44 and module housing 46. Main optical module 48, supplemental optical module 52 and supplemental optical module 56 are contained within module housing 46. Optical modules 48, 52 and 56 produce optical output beams 43, 49, 53 and 57, respectively, that sequentially excite different process chambers of disk 13. In other words, output beams 43, 49, 53 and 57 follow the curvature of disk 13 to each excite the same radial position of the disk which contains the process chambers. Optical module 48 contains two optical channels which each output different beams 43 and 49. Slot sensor trigger 27 includes infrared light source 31 which produces light 35 that is detected by detector 33.

Each of optical modules 48, 52 and 56 includes a respective release lever 50, 54 or 58, respectively, for engaging module housing 46. Each release lever may provide an upward bias to engage a respective latch formed within module housing 46. A technician or other user depresses release levers 50, 54 or 58, respectively, in order to unlatch and remove optical module 48, 52 or 56 from module housing 46. Barcode reader 29 includes laser 62 for identifying disk 13.

Base arm 44 extends from detection device 10 and provides support for module housing 46 and optical modules 48, 52 and 56. Module housing 46 may be securely mounted atop base arm 44. Module housing 46 may contain a location adapted to receive a respective one of optical modules 48, 52 and 56. Although described for exemplary purposes with respect to module housing 46, module housing 46 of detection device 10 may have a plurality of locations for receiving optical modules 48, 52 and 56. In other words, a separate housing need not be used for optical modules 48, 52 and 56.

Each location of module housing 46 may contain one or more tracks or guides which help to correctly position the associated optical module within the location when a technician or other user inserts the optical module. These guides may be located along the top, bottom, or sides of each locations. Each of optical modules 48, 52 and 56 may include guides or tracks that mate with the guides or tracks of the locations of module housing 46. For example, module housing 46 may have protruding guides which mate with recessed guides in optical modules 48, 52 and 56.

In some embodiments, module housing 46 may not completely enclose each of optical modules 48, 52 and 56. For example, module housing 46 may provide mounting points to secure each of optical modules 48, 52 and 56 to base arm 44, but portions or all of each optical module may be exposed. In other embodiments, module housing 46 may completely enclose each of optical modules 48, 52 and 56. For example, module housing 46 may include a single door that closes over optical modules 48, 52 and 56, or a respective door for each of the modules. This embodiment may be appropriate for applications where the modules are seldom removed or detection device 10 is subjected to extreme environmental conditions.

A technician may easily remove any of optical modules 48, 52 or 56, and this may be completed by using only one hand. For example, the technician may rest his or her forefinger under a molded lip located beneath release lever 54 of optical module 52. The technician's thumb may then press down release lever 54 to release optical module 52 from module housing 46. While grasping optical module 52 between the thumb and forefinger, the technician may pull back on the optical module to remove the optical module from detection device 10. Other methods may be used to remove any of optical module 48, 52 or 56, including methods utilizing two-handed removal. Inserting any of optical module 48, 52 or 56 may be accomplished in a reversed manner with one or two hands.

In the example of FIG. 3, the components of two optical modules are combined to form main optical module 48. Main optical module 48 may contain light sources that produce two different wavelengths of light and detectors for detecting each different wavelength of fluorescence from the samples in disk 13. Therefore, main optical module 48 may connect to two legs of fiber optic bundle 14. In this manner, main optical module 48 may be viewed as a dual-channeled optical module having two independent optical excitation and collection channels. In some embodiments, main optical module 48 may contain optical components for more than two optical modules. In other cases, module housing 46 contains a plurality (e.g., two or more) of single-channeled optical modules, such as supplemental optical modules 52 and 56.

As illustrated in FIG. 3, main optical module 48 may also contain components for a laser valve control system 51 (located within optical module 48). Laser valve control system 51 detects disk 13 location by a small slot located near the outer edge of disk 13. A detector (not shown) detects low power laser light 55 to map the location of disk 13 with respect to the motor which spins the disk. The control unit 23 uses the map to locate valves (not shown in FIG. 3) on disk 13 and to rotate targeted valves in position for opening via laser valve control system 51.

Once a targeted valve is in position, laser valve control system 51 focuses laser light 55 on the valve using one or more short bursts of high power. The short bursts form a void in the targeted valve, e.g., by piercing, melting or ablating the valve, allowing contents of an inner holding chamber to flow to an outer process chamber as disk 13 rotates. Detection device 10 may then monitor the subsequent reaction in the process chamber. Contents within a chamber may include substances in a fluid or solid state.

In some embodiments, laser valve control system 51 may be contained within a single-channeled optical module, e.g., supplemental optical module 54 or supplemental optical module 56. In other embodiments, laser valve control system 51 may be mounted to detection device 10 separately from any of optical modules 48, 52 or 56. In this case, laser valve control system 51 may be removable and adapted to engage a location within module housing 46 or a different housing of detection device 10.

In the example of FIG. 3, slot sensor trigger 27 is located near the removable modules, on either side of disk 13. In one embodiment, slot sensor trigger 27 contains a light source 31 to emit infrared (IR) light 35. Detector 33 detects IR light 35 when the slot in disk 13 allows the light to pass through the disk to detector 33. Control unit 23 uses an output signal produced by detector 33 to synchronize data acquisition from optical modules 48, 54 and 56 with rotation of disk 13. In some embodiments, slot sensor trigger 27 may extend from base arm 44 to reach the outer edge of disk 13 during device 10 operation. In other embodiments, a mechanical detector may be used to detect the position of disk 13.

Barcode reader 29 uses laser 62 to read a barcode located on the side edge of disk 13. The barcode identifies the type of disk 13 to allow proper operation of device 10. In some embodiments, the barcode may identify the actual disk to assist a technician in tracking data to specific samples from multiple disks 13.

All surface components of optical modules 48, 52 and 56 may be constructed of a polymer, composite, or metal alloy. For example, high molecular weight polyurethane may be used in forming the surface components. In other cases, an aluminum alloy or carbon fiber structure may be created. In any case, the material may be resistant to heat, fatigue, stress, and corrosion. As detection device 10 may come into contract with biological materials, the structures may be sterilizable in the event chamber contents leak out of disk 13.

Figure 4:
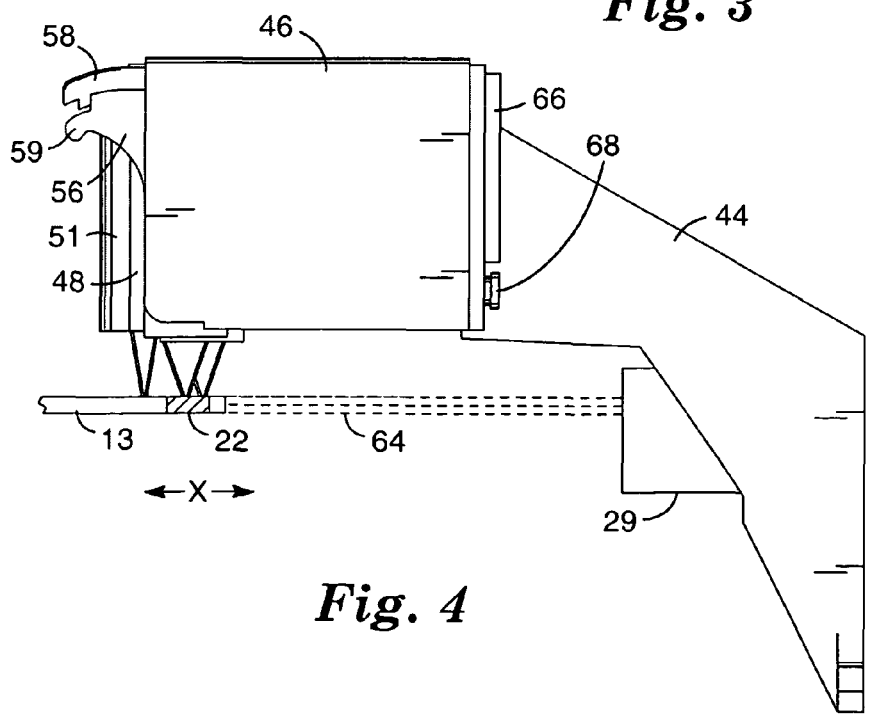
FIG. 4 is an perspective diagram illustrating the exemplary set of removable optical modules within the device housing.

FIG. 4 is an perspective diagram illustrating the exemplary set of removable optical modules 48, 52 and 56 within module housing 46 of detection device 10. In the example of FIG. 4, base arm 44 supports barcode reader 29 as well as the removable optical modules 48, 52 and 56 attached within module housing 46. Disk 13 is located beneath optical modules 48, 52 and 56 with the samples 22 located under a respective optical path of each of the modules at different moments in time.

Within module housing 46, the fronts of supplementary module 56 and main optical module 48 can be seen. Supplementary module 56 contains molded lip 59 and release lever 58. As previously described, molded lip 59 may be used to grasp module 56 when removing or inserting the module into module housing 46. All of optical modules 48, 52 and 56 may have a respective molded lip and release lever, or a single release lever may be used to remove all of the optical modules. In some embodiments, optical modules 48, 52 and 56 may contain a different component for grasping the module. For example, each of optical modules 48, 52 and 56 may contain a handle for removing the respective module in a vertical or horizontal direction from module housing 46.

The location of optical modules 48, 52 and 56 within module housing 46 may be fixed in order to separately excite different samples within disk 13 at any particular moment in time. For example, main optical module 48 may be located slightly further toward base arm 44 than supplemental optical modules 52 and 56, which are offset to a location at either side of the main module. Moreover, optical modules 48, 52 and 56 may be offset in a horizontal direction (indicated by the arrow in FIG. 4, where X is the distance the outside light beams are offset from the inside light beams) so that the excitation light beams produced by the modules follows the curvature of disk 13. In this arrangement, the light beams produced by optical modules 48, 52 and 56 traverse the same path as disk 13 rotates, thereby exciting and collecting light from process chambers located along the path. In other embodiments, optical modules 48, 52 and 56 are aligned such that the excitation light beams traverse different paths around rotating disk 13.

In this example, base arm 44 contains electrical contact board 66 which extends into module housing 46. Inside module housing 46, electrical contact board 66 may contain electrical contacts for each of optical modules 48, 52 and 56. Electrical contact board 66 may be electrically coupled to control unit 23. In some embodiments, each of optical modules 48, 52 and 56 may have a separate associated electrical contact board which is connected to control unit 23.

Fiber optic coupler 68 couples one leg of the fiber optic bundle 14 to an optical output port of optical module 56. Although not shown, each of optical modules 48, 52 and 56 include an optical output port adapted to engage a respective fiber optic coupler mounted to module housing 46. The connection between fiber optic coupler 68 and the leg of fiber optic bundle 14 may be a threaded screw lock, snap closure or friction fit.

Barcode reader 29 produces laser light 64 for reading the barcode of disk 13. The laser light 64 follows a direct path where it interacts with the outer edge of disk 13. The light 64 may spread out to cover a large area of disk 13 at one time. Barcode reader 29 reads the barcode on disk 13 when the disk is rotating at slow speeds. In other embodiments, barcode reader 29 may read the barcode periodically during operation to make sure a new disk has not been loaded in device 10. The barcode reader 29 may detect more than one barcode on disk 13 in other embodiments.

In some embodiments, base arm 44 may be movable with respect to disk 13. In this case, base arm 44 could be configurable to detect samples on different sized disks or samples located within an interior of disk 13. For example, a larger disk containing more process chambers or larger process chambers may be used by moving the base arm 44 further away from the center of disk 13. Module housing 46 may also have a configurable position for each of optical module 48, 52 or 56 so that each module may be movable to one or more circular paths of process chambers around disk 13.

Figure 5:
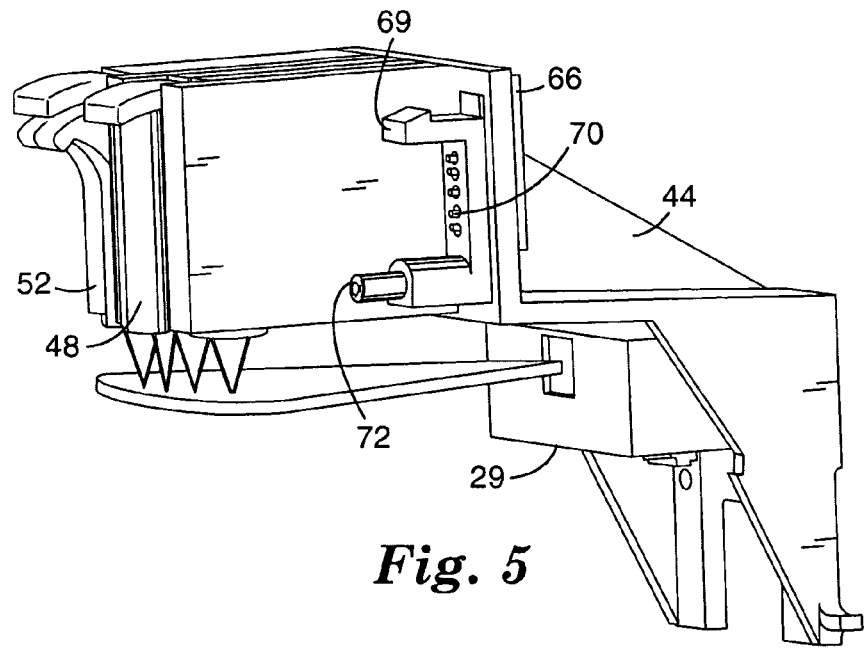
FIG. 5 is perspective diagram illustrating a front side view of an exemplary set of removable optical modules having one module removed to expose a module connector.

FIG. 5 is perspective diagram illustrating a front side view of an exemplary set of removable optical modules having one module removed to expose a module connector. In particular, module housing 46 is not shown in FIG. 5, and optical module 56 has been removed to expose optical modules 52 and 48 along with the connections for removed module 56.

Release lever 58 (FIG. 3) of optical module 56 securely attaches to attachment post 69 mounted to base arm 44. In this example, attachment post 69 extends into optical module 56 and couples to release lever 58. In other embodiments, other attachment mechanisms may be used to fix optical module 56 to base arm 44, such as a screw or snap fixation device.

Base arm 44 provides two different operational connections within module housing 46 for receiving and engaging optical module 56, once inserted. In particular, base arm 44 provides electrical contact board 66, which includes electrical connections 70 for coupling to the electrical contacts (not shown) contained within optical module 56. Electrical connections 70 allow control unit 23 to communicate with electrical components within module 56. For example, module 56 may include electrical circuits, hardware, firmware, or any combination thereof. In one example, the internal electrical components may store and output to control unit 23 unique identification information, such as a serial number. Alternatively, or in addition, the electrical components may provide information describing the specific characteristics of the optical components contained within the removable module 56. For example, the electrical components may include programmable read-only memory (PROM), flash memory, or other internal or removable storage media. Other embodiments may include a set of resistors, a circuit or an imbedded processor for outputting a unique signature of optical modules 48, 52 or 56 to control unit 23. In another example, optical module 56 may include a laser source and other components that form part of a laser valve control system, i.e. laser valve control system 51.

Electrical contact board 66 may be removed and replaced with another version associated with a different removable optical module. This option may support upgrades in device capability. In other embodiments, connections 70 may contain more or less connection pins.

In addition, base arm 44 and module housing 46 provide optical channel 72 within the location for receiving optical module 56. Optical channel 72 is connected to fiber optic coupler 68 (FIG. 4) that interfaces with a leg of fiber optic bundle 14. Optical channel 72 inserts into a location within optical module 56. The light captured by optical module 56 may be directed through optical channel 72, fiber optic coupler 68 and fiber optic bundle 15 to the detector. Fittings between these connections may be tight to ensure that light does not escape or enter the optical path.

In some embodiments, the connections to optical module 56 may be arranged in a different configuration. For example, the connections may be located in another position for accepting optical module 56 from another direction. In other embodiments, electrical connections may be located on one side of optical module 56 while an optical connection is located on a second surface of module 56. In any case, the electrical and optical connections located within the location of module housing 46 accommodate a removable optical module, i.e., optical module 56 in this example.

The optical and electrical connections of module 56 described in FIG. 5 may be used with any module, including optical modules 48 and 52. In addition, the connections for each optical module may not be identical. Since connections may be modified for coupling with a desired removable optical module, the connections utilized by any particular optical module inserted within a particular location of module housing 46 may vary at any time.

Figure 6:
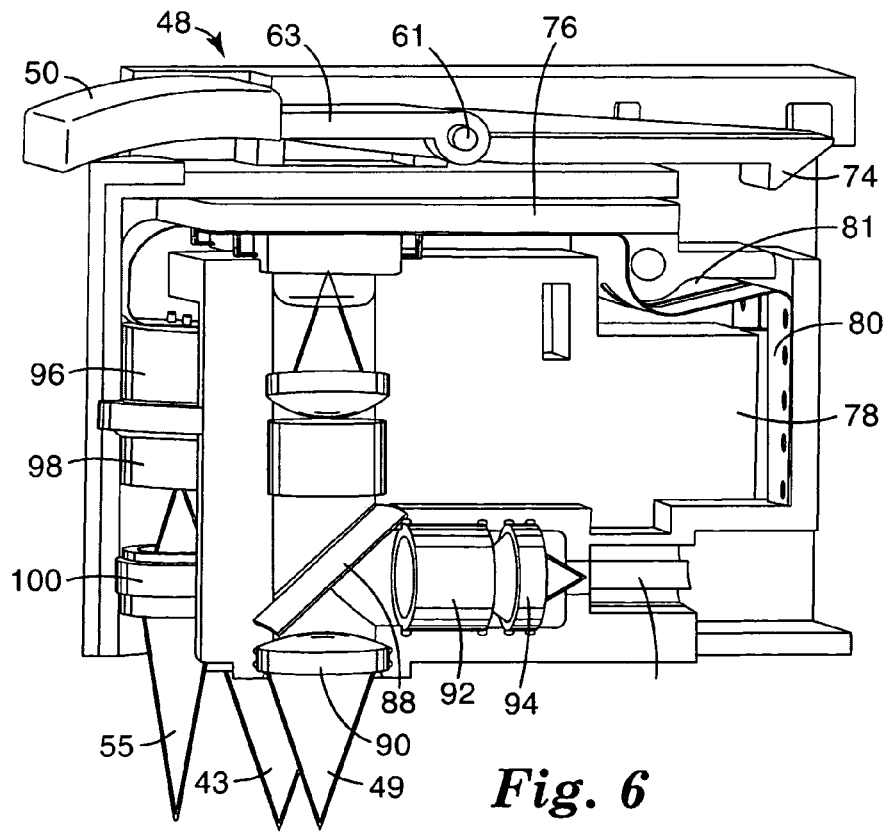
FIG. 6 is perspective diagram illustrating the components within an exemplary main removable optical module.

FIG. 6 is perspective diagram illustrating the components within an exemplary main removable optical module 48. In the example of FIG. 6, main optical module 48 includes release lever 50, pivot pin 61 and latch 74. Internal housing 78 separates each side of module 48 and contains electrical contacts pad 80 connected to ribbon 81. Optical components include LED 82, collimating lens 84, excitation filter 86, dichroic filter 88, focusing lens 90, detection filter 92 and lens 94. Optical output port 17 couples to a leg of fiber optic bundle 14. A separate set of optical components for a second optical channel (not shown) are located on the other side of internal housing 78. In addition, main module 48 includes connector 96, laser diode 98 and focusing lens 100 as part of a laser valve control system 51 controlled by control unit 23.

Release lever 50 is attached to optical module 48 by a pivot pin 61. Pivot pin 61 allows release lever 50 to rotate about the axis of the pin. When release lever 50 is depressed, arm 63 rotates counter-clockwise to raise latch 74. Once latch 74 is raised, optical module 48 may be free for removal from module housing 46. There may be a spring or other mechanism maintaining a bias force against release lever 50 to maintain latch 74 in a down position. In some embodiments, a spring may be included around pivot pin 61 to provide a moment arm that keeps latch 74 in the down, or latched, position. In other embodiments, other mounting mechanisms may be added to or used in place of the described lever. For example, optical module 48 may be attached to module housing 46 by one or more screws or pins.

Mounting board 76 may be installed within optical module 48 for attaching communication ribbon 81 and LED 82. Ribbon 81 is connected to electrical contacts pad 80 and provides a connection between the pad and electrical components within optical module 48. Contacts pad 80 and ribbon 81 may carry the information required for both sides of main optical module 48, including laser valve control system 51 and any internal memory or other storage medium. Ribbon 81 may be flexible for weaving within optical module 48. Ribbon 81 may contain a plurality of electrically conductive wires to communicate signals between the electrical components and control unit 23 and/or to deliver power to the electrical components. In some embodiments, each electrical component may have a separate cable connecting the component with control unit 23. A technician may need to disconnect a cable or flex circuit from module housing 46 when removing optical module 48 from the housing.

In some embodiments, optical module 48 may contain a detector for detecting light from disk 13 and electronics for processing and storing the data. The electronics may contain a telemetry circuit for wirelessly transmitting data representing the detected light to control unit 23. Wireless communication may be performed by infrared light, radio frequency, Bluetooth, or other telemetry technique. Optical module 48 may also include a battery to power the electronics, which may be rechargeable by control unit 23.

LED 82 is affixed to mounting board 76 and electrically coupled to ribbon 81. LED 82 produces excitation light 49 of a predetermined wavelength to excite the sample 22. Excitation light 43 is produced by the second optical channel (not shown). After light 49 leaves LED 82, the light is expanded by collimating lens 84 before the light enters excitation filter 86. The light 49 of one wavelength band is passed by dichroic filter 88 and is focused on a sample by focusing lens 90. The light 49 excites the sample and fluorescence is collected by focusing lens 90 and delivered to detection filter 92 by dichroic filter 88. The resulting wavelength band of light is collected by lens 94 and delivered to optical output port 17 where the collected fluorescent light enters a leg of fiber optic bundle 14 for conveyance to detector 18.

Internal housing 78 may support all components included in the excitation of the sample and detection of fluorescent light emitted by the sample for a selected wavelength. On the other side of internal housing 78, a similar configuration of optical components may be included to produce light of a different wavelength and detect the corresponding different fluorescent wavelength. Separation of each side may eliminate light contamination from one side entering the optical channel of the other side.

Housed partially between each side of module 48 may be the components of laser valve control system 51, including connector 96, laser diode 98 and focusing lens 100. Internal housing 78 may provide physical support for these components. Ribbon 81 is connected to connector 96 for communicating drive signals and power to the laser source. Laser diode 98 is connected to connector 96 and produces the laser energy 55 used to open valves on disk 13. Laser diode 98 delivers this near-infrared (NIR) light to focusing lens 100 for directing the laser energy 55 to specific valves on disk 13. An NIR sensor may be located below disk 13 for locating particular valves that need to be opened. In other embodiments, these components may be housed separately from the optical components.

In some embodiments, emission lens 98 and focusing lens 100 of laser valve control system 51 may be contained within a single-channeled optical module, such as supplemental optical module 52 and 56 (FIG. 3).

Figure 7:
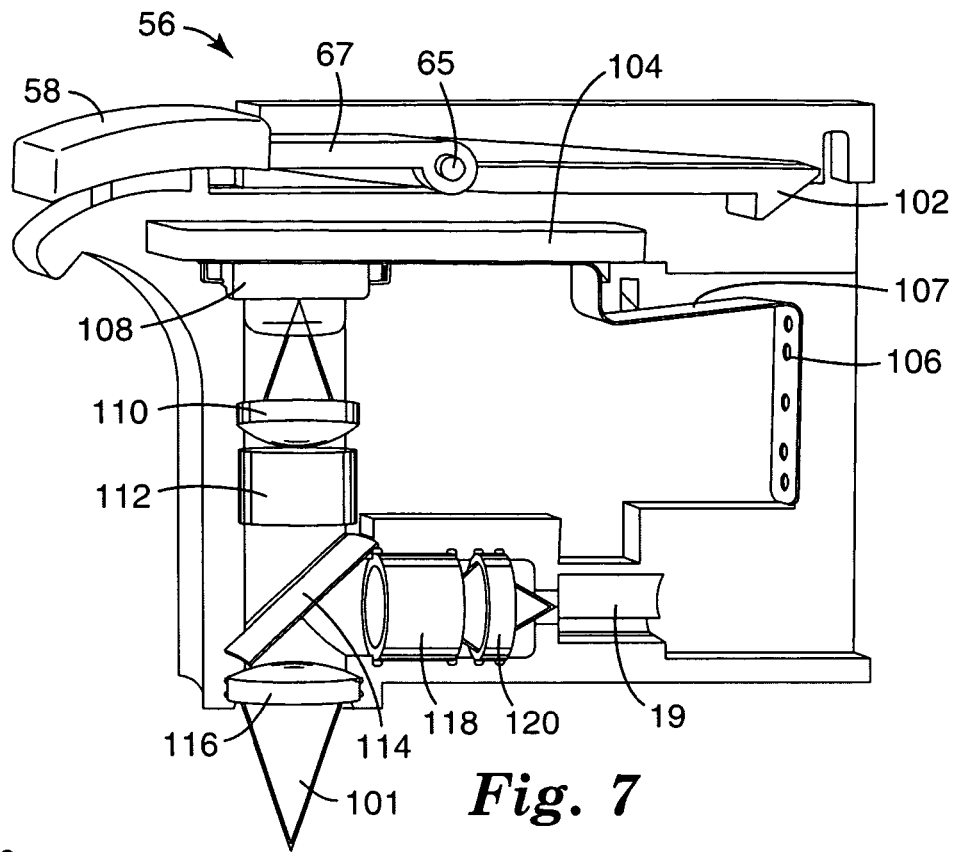
FIG. 7 perspective diagram illustrating the components within an exemplary supplemental removable optical module.

FIG. 7 is a perspective diagram illustrating the components within an exemplary supplemental optical module that may be easily removed from or inserted into detection device 10. In the example of FIG. 7, optical module 56 includes release lever 58, pivot pin 59 and latch 102, similar to main optical module 48. Optical module 56 also includes electrical contacts pad 106 connected to ribbon 107. Ribbon 107 may also be connected to mounting board 104. Similar to main optical module 48, optical components include LED 108, collimating lens 110, excitation filter 112, dichroic filter 114, focusing lens 116, detection filter 118 and lens 120. Optical output port 19 couples to a leg of fiber optic bundle 14.

Release lever 58 is attached to optical module 56 by a pivot pin 65. Pivot pin 65 allows the release lever to rotate about the axis of the pin. When release lever 58 is depressed, arm 67 rotates counter-clockwise to raise latch 102. Once latch 102 is raised, optical module 56 may be free for removal from module housing 46. There may be a spring or other mechanism maintaining a bias force against release lever 58 to maintain latch 102 in a down position. Alternatively, a spring may be located above latch 102. In some embodiments, a spring may be included around pivot pin 65 to provide a moment arm that keeps latch 102 in the down, or latched, position. In other embodiments, other mounting mechanisms may be added to or used in place of the described lever. For example, optical module 56 may be attached to module housing 46 by one or more screws or pins.

Mounting board 104 may be installed within optical module 56 for attaching communication ribbon 107 and LED 108. Ribbon 107 is connected to electrical contacts pad 106 and provides a connection between the pad and electrical components within optical module 56. Contacts pad 106 and ribbon 107 may carry the information required for operating the optical components. Ribbon 107 may be flexible for weaving within optical module 56. Ribbon 107 may contain a plurality of electrically conductive wires to communicate signals between the components and control unit 23 and/or deliver power to the electrical components. In some embodiments, each electrical component may have a separate cable connecting the component with control unit 23. A technician may need to disconnect a cable or flex circuit from module housing 46 when removing optical module 56 from the housing.

In some embodiments, optical module 56 may contain a detector for detecting light from disk 13 and electronics for processing and storing the data. The electronics may contain a telemetry circuit for wirelessly transmitting data representing the detected light to control unit 23. Wireless communication may be performed by infrared light, radio frequency, Bluetooth, or other telemetry technique. Optical module 56 may also include a battery to power the electronics, which may be rechargeable by control unit 23.

LED 108 is affixed to mounting board 104 and electrically coupled to ribbon 107. LED 108 produces excitation light 101 of a predetermined wavelength to excite the sample 22. After light 101 leaves LED 108, the light is expanded by collimating lens 110 before the light enters excitation filter 112. The light 101 of one wavelength band is passed by dichroic filter 114 and is focused on a sample by focusing lens 116. The light 101 excites the sample and fluorescence is collected by focusing lens 116 and delivered to detection filter 118 by dichroic filter 114. The resulting wavelength band of light is collected by lens 120 and delivered to optical output port 19 where the collected fluorescent light enters a leg of fiber optic bundle 14 for conveyance to detector 18.

Supplemental optical module 56 may also contain the components of laser valve control system 51. Laser valve control system 51 may be the only system used within device 10 or one of a plurality of laser valve control systems. The components used for this system may be similar to the components described in optical module 48 of FIG. 6.

The components of supplemental optical module 56 may be similar to any supplemental optical module or any optical module used to emit and detect one wavelength band of light. In some embodiments, the components may be altered in configuration to accommodate different experimental applications. For example, any optical modules may be modified to be inserted from a different direction or to be placed within the device at a different position with respect to disk 13. In any case, the optical modules may be removable to provide modification flexibility to device 10.

Figure 8:
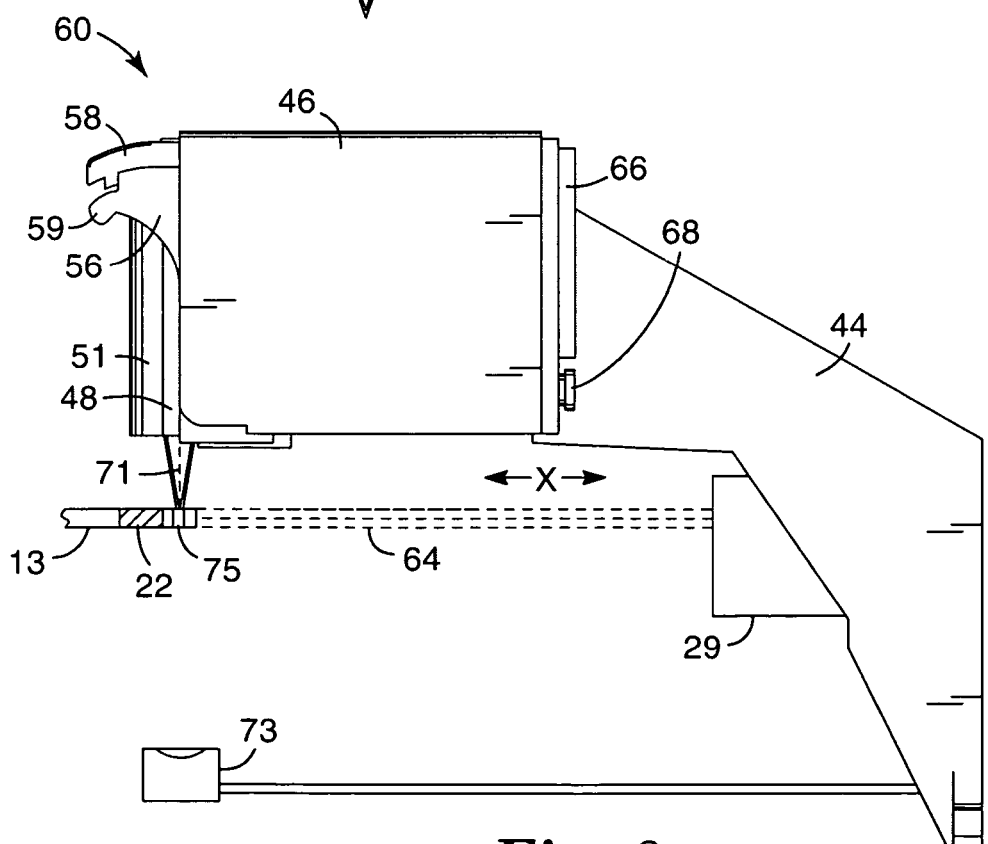
FIG. 8 is an illustration of the side view of an exemplary set of removable optical modules within the device housing with the laser valve control system located over a slot on the disk.

FIG. 8 is an illustration of the side view of an exemplary set of removable optical modules 48, 52 and 56 within the device housing with the laser valve control system located over a slot on the disk. The example of FIG. 8 is similar to FIG. 4. However, laser valve control system 51 has been positioned to aim laser light 71 from an energy source, i.e. a laser diode, through slot 75 in disk 13. Sensor 73 detects laser light 71 when the light passes through slot 75.

A gantry 60 moves module housing 46 and the contained optical modules 48, 52 and 56 in a horizontal direction (shown as arrows on FIG. 8) relative to a center of disk 13. Laser light 71 may be emitted by the laser at a reduced current to produce low power near-infrared (NIR) light for locating slot 75 in disk 13. In some cases, the gantry 60 may translate module housing 46 in the horizontal direction while laser valve control system 51 outputs laser light 71 in order to locate slot 75.

Sensor 73 may detect laser light 71 once the laser light travels through slot 75, causing sensor 73 to output an electrical signal representative of the sensed NIR laser light 71 to control unit 23. Upon receiving the electrical signal from sensor 73, control unit 23 maps the sensed disk position to a known location of rotating platform 25 and constructs a position map that identifies the position of each valve of disk 13 relative to the known position of rotating platform 25. Control unit 23 may subsequently use the constructed position map to move the laser, rotate the disk, or both, so as to target the desired valves of disk 13. In other embodiments, sensor 73 may be located on the same side of disk 13 as laser valve control system 51 to detect laser light 71 from a reflective portion or portions of disk 13.

Upon positioning laser valve control system 51 over a selected valve, control unit 23 directs the laser valve control system to deliver short pulses of high-power energy to open the selected valve. Valves may be constructed out of a polymer or similar material that absorbs the emitted electromagnetic energy, i.e., laser light 71, causing the polymer to rupture, thereby opening a channel between an inner holding chamber and an outer process chamber. Other energy sources may be used (e.g., radio frequency energy sources), and materials may be selected that absorb the produced energy and rupture (i.e., open). Once the valves are opened, rotation of disk 13 directs contents of the respective inner holding chamber to the respective outer process chamber.

In some embodiments, laser valve control system 51 and slot sensor trigger 27 may communicate for effective positioning of disk 13. For example, slot sensor trigger 27 may generally locate the radial position of disk 13 by sensing the presence of slot 75. Laser valve control system 51 may specifically detect each of the edges of slot 75 for a more accurate radial and angular position of disk 13. As the edges of slot 75 are smaller features than slot 75, laser valve control system 51 may provide a higher spatial resolution detection system than slot sensor trigger 27. Alternatively, slot sensor trigger 27 may be able to provide higher temporal resolution as slot 75 position may be detected at high rotational speeds. Edges of slot 75 may be undetectable by laser valve control system 51 at high rotational speeds.

Further, some embodiments may not include a gantry 60 to horizontally move components for aligning light paths with structures on disk 13. For example, laser valve control system 51 and optical modules 48, 52 and 56 may be fixed at appropriate radial distances from a center of disk 13. As another example, laser valve control system 51 and/or optical modules 48, 52 and 56 may pivot under the direction of control unit 23 to aim laser light at different radial positions of disk 13.

Figure 9A:
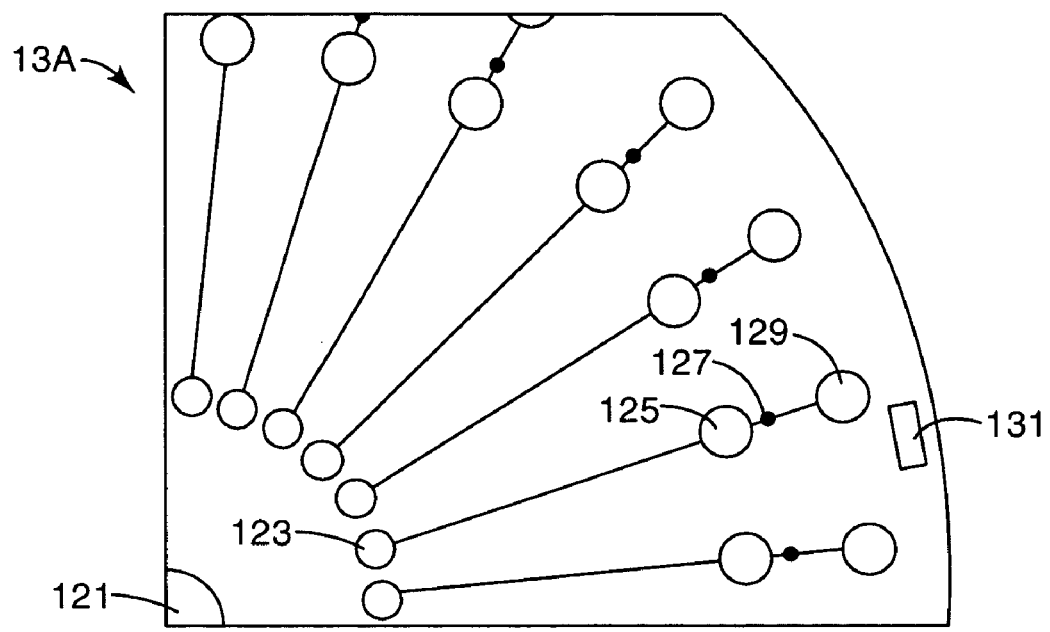
FIGS. 9A, 9B, and 9C illustrate the chambers and valves of three exemplary disks that may be used to hold samples within the detection device.
Figure 9B:
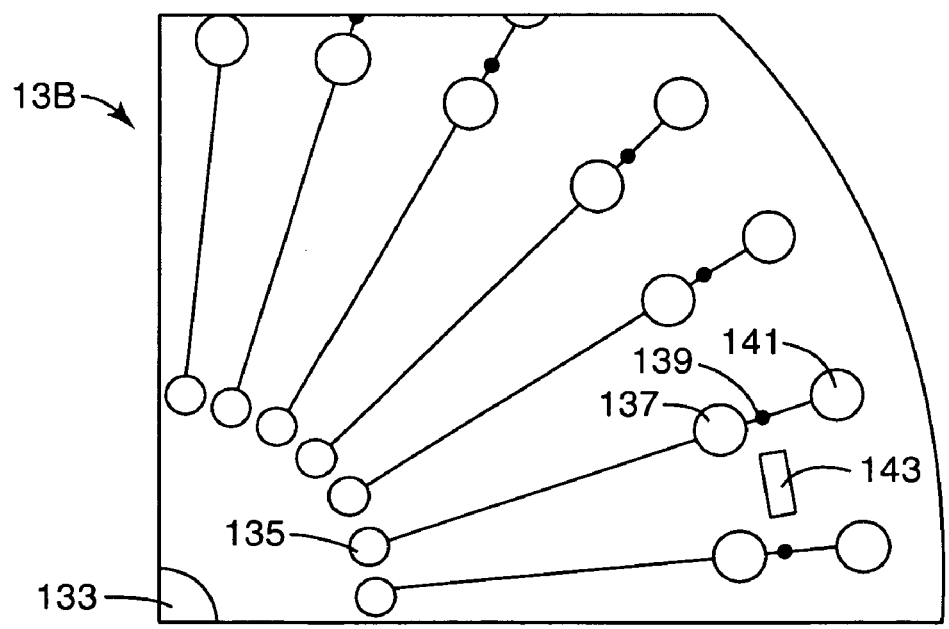
Figure 9C:
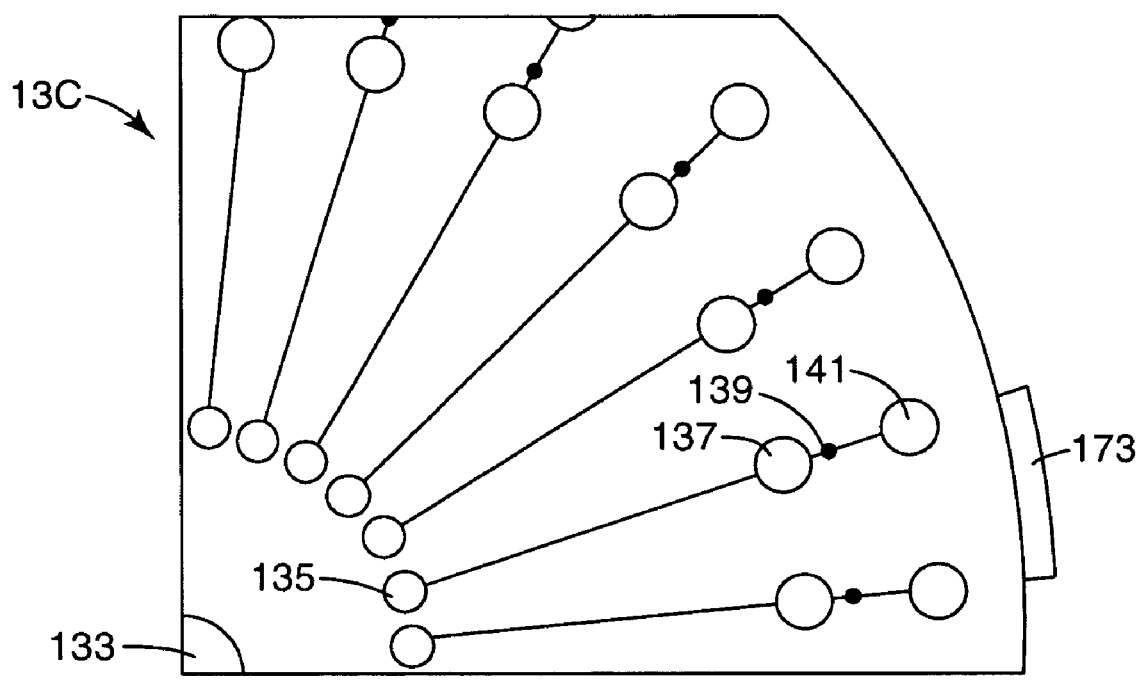

FIGS. 9A, 9B, and 9C are schematic diagrams illustrating portions of exemplary disks 13A, 13B, and 19C, respectively. In the example if FIG. 9A, disk 13A includes a center hole 121 for attaching the disk to a rotating platform of device 10. A set of inner holding chambers and a set of outer process chambers are concentrically located radially from center hole 121. In this example, each chamber is illustrated to have identical volume and spacing; however, other embodiments of disk 13 may include chambers having different volumes and spacing.

In this example, each holding chamber is connected to a corresponding process chamber by a channel, and each channel contains a respective valve to control flow through the channel. For example, valve 127 separates holding chamber 125 from process chamber 129.

Some reagents of a sample may be directly placed within process chamber 129, while holding chamber 125 contents may be first loaded into loading chamber 123. The contents of loading chamber 123 may then be forced out to holding chamber 125 once the disk 13A is spun. In some embodiments, holding chamber 125 may be used to contain a reagent for a second reaction or an agent to deactivate the reaction in process chamber 129. Valve 127 is located between holding chamber 125 and process chamber 129.

In the example of FIG. 9A, slot 131 is positioned on the outside of disk 13A, and is used by laser valve control system 51 to map the disk position. In one embodiment, slot 131 is 1 mm in width by 2 mm in length. Laser light 71 (FIG. 8) may be focused at known radius of disk 13A corresponding to a known radial location of slot 131. As disk 13A is spun, laser light 71 is blocked by disk 13A except at the location of slot 131, where the light passes through disk 13A and is detected by sensor 73 (FIG. 8). As described above, control unit 23 utilizes an output signal (e.g., a trigger signal) received from sensor 73 to map the position of disk 13A relative to the rotation of rotating platform 25. Laser valve control system 51 detects the edges of slot 131 because the smaller feature of an edge enables the system to create a more accurate and higher resolution map of disk 13A position than using just the location of slot 131.

Based on the map, control unit 23 repositions laser valve control system 51 at a known radial distance for the valves, e.g., valve 127, from center hole 121. For example, a gantry 60 attached to module housing 46 may move the module housing 46 and the included optical modules to the known radial distance from the center of disk 13A for the valves. Control unit 23 then utilizes the map to control rotation of the rotating platform and disk 13 to rotate valve 127 directly under laser valve control system 51. Once in place, control unit 23 directs laser valve control system 51 to output a high current pulse of energy to heat valve 127. As a result, the heat forms a void in valve 127 (e.g., ruptures the valve) to open fluid communication between holding chamber 125 and process chamber 129. In other embodiments, heat from laser light 71 may change the conformation of valve 127 to open fluid communication.

FIG. 9B illustrates a section of another exemplary disk 13B, similar to disk 13A of FIG. 9A. In the example of FIG. 9B, disk 13B includes center hole 133 for attaching the disk to the base plate fixed to rotating platform 25. Again, each set of chambers is shown to have identical volume; however, other embodiments of disk 13B may include chambers having different volumes and spacing.

Disk 13B differs from disk 13A only in the position of slot 143 on the disk for use in tracking disk position. In particular, slot 143 is located at a slightly smaller radius from a center hole 133 of disk 13B than slot 131 is located from center hole 121 of disk 13A. In this example, control unit 23 may be able to perform tracking functions and valve opening functions without needing to radially reposition laser valve control system 51. For example, control unit 23 may place laser valve control system 51 in a low power mode to use a reduced or minimal current when outputting light 71 creating a map of disk 13B. The reduced current is insufficient to produce enough energy for opening any of the valves of disk 12B, but sufficient for detection by slot sensor 73. Control unit 23 may subsequently place laser valve control system 51 in a high power mode that utilizes a higher current to produce a higher intensity laser light sufficient to open a selected valve, e.g., valve 139, after creating the map of disk 13B and positioning the laser valve control system.

Generally, slot 131 (or slot 143 of FIG. 9A) may be located at any position of disk 13B (or 13A). In some embodiments, slot 143 may be located at or near an outermost edge of disk 13B. Alternatively, slot 143 may be located closer to the center than slot 131. Further, the shape of slot 143 need not be rectangular. The shape may be any polygon, circle, square, triangle, crescent or any irregular shape. Further disk 13B may contain more than one slot 143 for determining disk position, and the multiple slots may different from each other in radial distance from center hole 133, size or shape.

FIG. 9C, then, illustrates a disk 13C similar to those shown in FIGS. 9A and 9B. Disk 13C, however, includes a tab 173 in place of slot 131 and/or slot 143 to block the electromagnetic energy from the energy source to the sensor.

Generally, chambers and channels formed in disk 13 may be covered or uncovered. In some embodiments, more chambers and valves may be included on disk 13. Channels connecting the chambers may also be curved or meet other channels at certain chambers or intersection points. Since the disk 13 is three dimensional, chambers may lie in different planes, and channels may having varying depths.

Disk 13 may be constructed out of a biocompatible material suitable for spinning at high speeds. For example, disk 13 may be made out of polyethylene, polypropylene, polycarbonate, polyurethane, or some other moldable polymer. Disks 13 may be constructed by molding, layering, etching or other techniques. While the disks 13 may be approximately 120 mm in diameter, disks may also be of a plurality of sizes to accommodate multiple applications. Disk 13 size may be detected upon insertion into the detection device 10, read by barcode reader 29 via a bar code fixed to disk 13, or a technician may enter the type of disk 13 being used in the application. In some embodiments, the disks 13 may be able to be sterilized while other embodiments may utilize one time use consumable disks.

Figure 10:
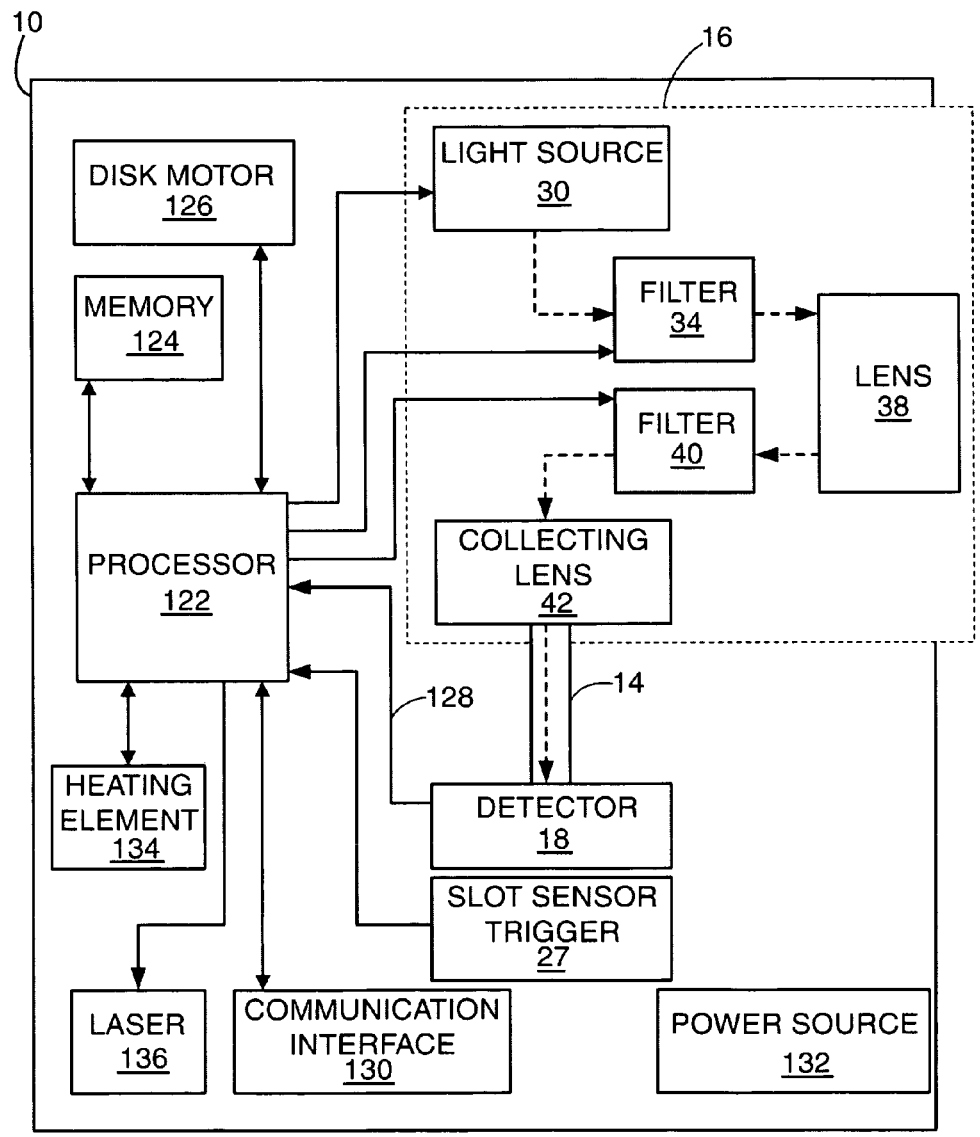
FIG. 10 is a block diagram illustrating an example embodiment of the multiplex fluorescence detection device in further detail.

FIG. 10 is a functional block diagram of the multiplex fluorescence detection device 10. In particular, FIG. 10 indicates the electrical connections between device components and the general paths of light through the components. In the example of FIG. 10, device 10 includes at least one processor 122 or other control logic, memory 124, disk motor 126, light source 30, excitation filter 34, lens 38, detection filter 40, collecting lens 42, detector 18, slot sensor trigger 27, communication interface 130, heating element 134, laser 136 and power source 132. As shown in FIG. 10, lens 38 and collecting lens 42 need not be electrically connected to another component. Further, light source 30, filters 34 and 40, lens 38 and collecting lens 42 are representative of one optical module 16. Although not illustrated in FIG. 10, device 10 may contain additional optical modules 16, as described previously. In that case, each additional optical module may include components arranged substantially similarly as to those shown in FIG. 10.

Light follows a certain path through several components in FIG. 10. Once light is emitted by light source 30, it enters excitation filter 34 and leaves as light of a discrete wavelength. It then passes through lens 38 where it leaves detection device 10 and excites sample 22 within a process chamber (not shown). Sample 22 responds by fluorescing at a different wavelength, at which time this light enters lens 38 and is filtered by detection filter 40. Filter 40 removes background light of wavelengths outside of the desired fluorescence from sample 22. The remaining light is sent through collecting lens 42 and enters a leg of fiber optic bundle 14 before being detected by detector 18. Detector 18 subsequently amplifies the received light signal.

Processor 122, memory 124 and communication interface 130 may be part of control unit 23. Processor 122 controls disk motor 126 to rotate or spin disk 13 as needed to collect fluorescence information or move fluid through disk 13. Processor 122 may use disk position information received from slot sensor trigger 27 to identify the location of chambers on disk 13 during rotation and synchronize the acquisition of florescence data received from the disk.

Processor 122 may also control when the light source 30 within optical module 16 is powered on and off. In some embodiments, processor 122 controls excitation filter 34 and detection filter 40. Depending on the sample being illuminated, processor 122 may change the filter to allow a different wavelength of excitation light to reach the sample or a different wavelength of fluorescence to reach collecting lens 42. In some embodiments, one or both filters may be optimized for the light source 30 of the particular optical module 16 and not changeable by processor 122.

Collecting lens 42 is coupled to one leg of fiber bundle 14 that provides an optical path for the light from the collecting lens to detector 18. Processor 122 may control the operation of detector 18. While detector 18 may constantly be detecting all light, some embodiments many utilize other acquisition modes. Processor 122 may determine when detector 18 collects data and may programmatically set other configuration parameters of detector 18. In one embodiment, detector 18 is a photomultiplier tube that captures fluorescence information from light provided by collecting lens 42. In response, detector 18 produces an output signal 128 (e.g., an analog output signal) representative of the received light. Although not shown in FIG. 10, detector 18 may concurrently receive light from other optical modules 16 of device 10. In that case, output signal 128 electrically represents a combination of the optical input received by detector 18 from the various optical modules 16.

Processor 122 may also control data flow from device 10. Data such as sampled fluorescence from detector 18, temperature of the samples from heating element 134 and related sensors, and disk rotation information may be stored into memory 124 for analysis. Processor 122 may comprise any one or more of a microprocessor, digital signal processor (DSP), application specific integrated circuit (ASIC), field-programmable gate array (FPGA), or other digital logic circuitry. Moreover, processor 122 provides an operating environment for firmware, software, or combinations thereof, stored on a computer-readable medium, such as memory 124.

Memory 124 may include one or more memories for storing a variety of information. For example, one memory may contain specific configuration parameters, executable instructions, and one may contain collected data. Therefore, processor 122 may use data stored in memory 124 for controlling device operation and calibration. Memory 124 may include any one or more of a random access memory (RAM), read-only memory (ROM), electronically-erasable programmable ROM (EEPROM), flash memory, or the like.

Processor 122 may additionally control heating element 134. Based upon the instructions contained within memory 124, the heating element 134 may be selectively driven to control the temperature of one or more chambers according to desired heating profiles. Generally, heating element heats one radial section of disk 13 as the disk spins. Heating element 134 may comprise a halogen bulb and reflector for focusing heating energy on a specific area of disk 13. In other embodiments, heating element 134 may heat one or more chambers sequentially. This embodiment would require disk 13 to be stationary while a chamber is heated. In any embodiment, heating element 134 may be capable of turning on and off extremely quickly as needed.

Laser 136 is used to control valve opening which allows contents of a holding chamber to flow to another chamber on disk 13, e.g., a process chamber. Processor 122 and supporting hardware drives laser 136 to selectively open specific valves contained with disk 13. Processor 122 may interact with a laser sensor underneath disk 13 for determining the position of the laser relative to the desired valve. When in position, processor 122 outputs signals to direct laser 136 to produce a burst of energy targeted at the valve. In some cases, the burst may last for approximately 0.5 seconds, while other embodiments may include opening times of shorter or greater duration. A laser energy and pulse duration may be controlled by processor 122 through communication with laser 136.

Processor 122 utilizes communication interface 130 to communicate with data acquisition system 21. The communication interface 130 may include a single method or combination of methods to transfer data. Some methods may include a universal serial bus (USB) port or IEEE 1394 port for hardwire connectivity with high data transfer rates. In some embodiments, a storage device may be directly attached to one of these ports for data storage for post processing. The data may be pre-processed by processor 122 and ready for viewing, or the raw data may need to be completely processed before analyzing can begin.

Communications with detection device 10 may also be accomplished by radio frequency (RF) communication or a local area network (LAN) connection. Moreover, connectivity may be achieved by direct connection or through a network access point, such as a hub or router, which may support wired or wireless communications. For example detection device 10 may transmit data on a certain RF frequency for reception by the target data acquisition device 21. Data acquisition device 21 may be a general purpose computer, a notebook computer, a handheld computing device, or an application-specific device. Further, multiple data acquisition devices may receive the data simultaneously. In other embodiments, the data acquisition device 21 may be included with detection device 10 as one integrated detection and acquisition system.

In addition, detection device 10 may be able to download updated software, firmware, and calibration data from a remote device over a network, such as the internet. Communication interface 130 may also enable processor 122 to monitor inventory report any failures. If operational problems occur, processor 122 may be able to output error information to assist a user in trouble shooting the problems by providing operational data. For example, processor 122 may provide information to help the user diagnose a failing heating element or a synchronization problem.

Power source 132 delivers operating power to the components of device 10. Power source 132 may utilize electricity from a standard 115 Volt electrical outlet or include a battery and a power generation circuit to produce the operating power. In some embodiments, the battery may be rechargeable to allow extended operation. For example, device 10 may be portable to detection of biological samples in an emergency, such as a disaster area. Recharging may be accomplished through the 115 Volt electrical outlet. In other embodiments, traditional batteries may be used.

Figure 11:
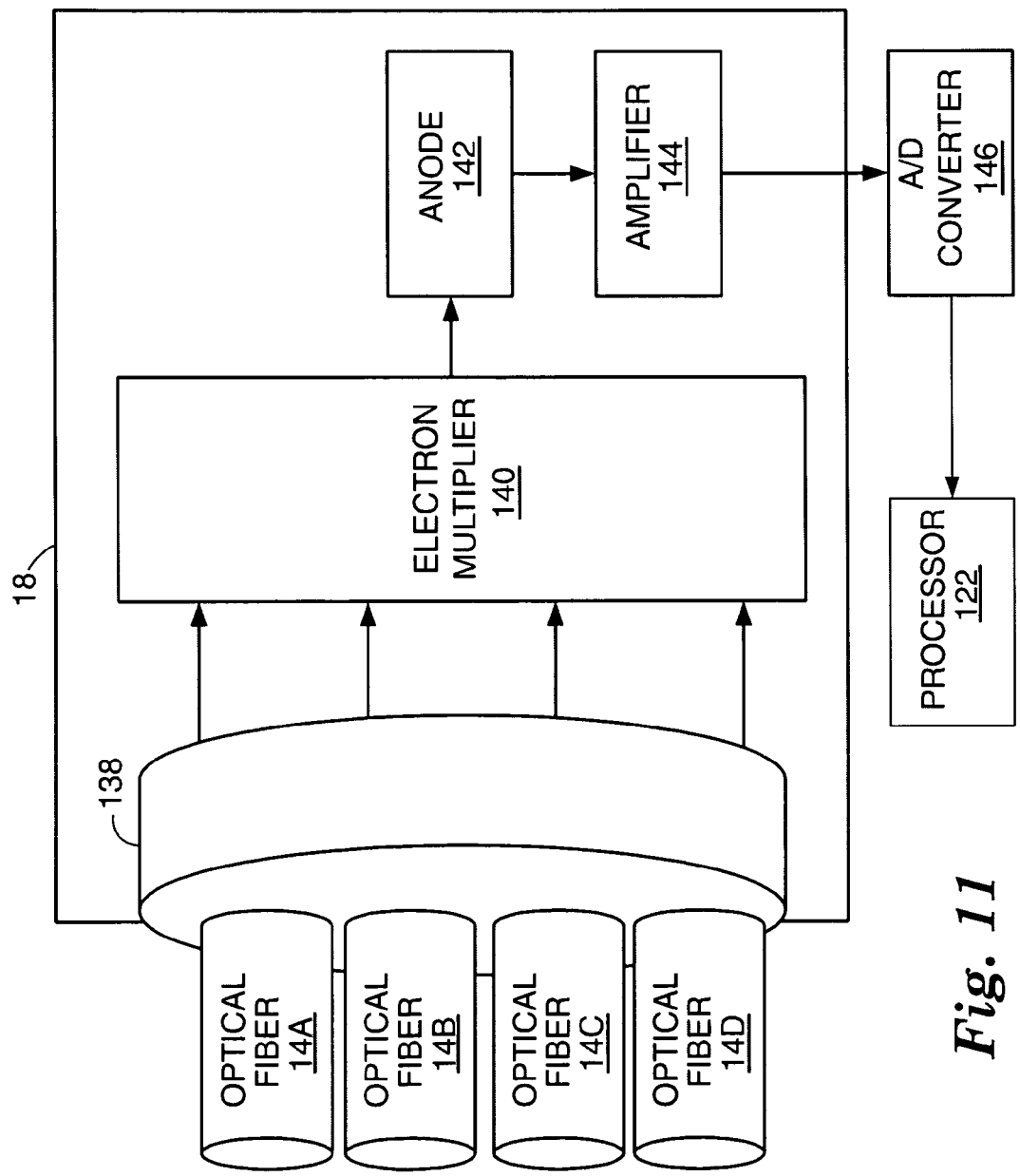
FIG. 11 is a block diagram of the a single detector coupled to four optical fibers of the optical fiber bundle.

FIG. 11 is a functional block diagram of the single detector 18 coupled to four optical fibers of the optical fiber bundle. In this embodiment, detector 18 is a photomultiplier tube. Each leg of fiber optic bundle 14, optical fiber 14A, optical fiber 14B, optical fiber 14C and optical fiber 14D, couples to an optical input interface 138 of detector 18. In this manner, light carried by any of optical fibers 14 is provided to a single optical input interface 138 of detector 18. The optical input interface 138 provides the aggregate light to electron multiplier 140. Anode 142 collects the electrons and produces a corresponding analog signal as output signal.

In other words, as shown, the optical fibers 14 fit within the input optical aperture for detector 18. Consequently, detector 18 may be used to detect light from each leg of optic bundle 14 simultaneously. Optical input interface 138 provides the light to electron multiplier 140. For a photomultiplier tube, the photons from the optical fibers first hit a photoemissive cathode, which in turn releases photoelectrons. The photoelectrons then cascade by hitting a series of dynodes, more photoelectrons being emitted upon contact with each dynode. The resulting group of electrons have essentially multiplied the small light signals originally transmitted by the optical fibers 14. The increased number of electrons finally are collected by anode 142. This current from anode 142 is transferred by a current to voltage amplifier 144 as an analog output signal which is representative of the optical florescent signals from the sample provided by the plurality of optical modules 16.

Control unit 23 includes an analog to digital (A/D) converter 146 converts the analog signal to a stream of sampled digital data, i.e., a digital signal. Processor 122 receives the digital signal and stores the sampled data in memory 124 for communication to data acquisition device 21, as described in above. In some embodiments, A/D converter 146 may be contained within detector 18 instead of control unit 23.

In this manner, a single detector 18 may be utilized to collect all light from the optic bundle 14 and produce a signal representative thereof. Once the signal is amplified by amplifier 144 and converted to a digital signal, it may be digitally separated into data corresponding to the light collected by each individual optical modules 16. The entire (i.e., aggregate) signal may be separated by frequency range into each detected signal representative of each fluorescence. These frequencies may be separated by a digital filter applied by data acquisition device 21 or within device 10.

In other embodiments, the amplified signal may be separated by frequency using analog filters and sent to separate channels before A/D converter 146. Each channel may then be separately digitized and sent to the data acquisition device. In either case, the single detector is able to capture all florescence information from each optical module 16. Data acquisition device 21 may then plot and analyze the signal acquired from each well of disk 13 in real-time without the need for multiple detectors.

In some embodiments, detector 18 may not be a photomultiplier tube. In general, detector 18 may be any type of analog or digital detection device capable of capturing light from multiple legs of an optical delivery mechanism, i.e., fiber bundle 14, and producing a transmittable representation of the captured light.

Figure 12:
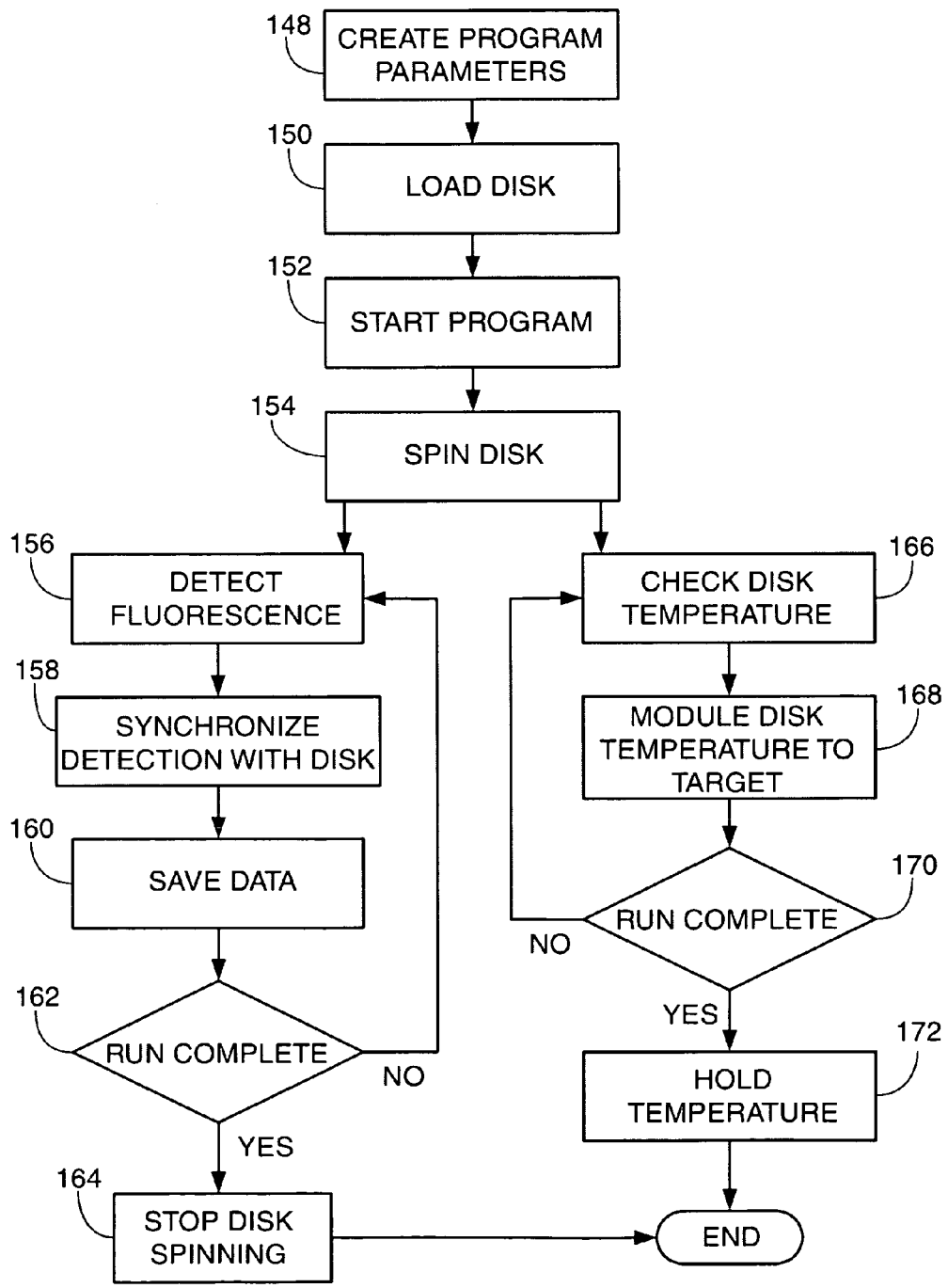
FIG. 12 is a flow diagram illustrating exemplary operation of the multiplex fluorescence detection device.

FIG. 12 is a flow diagram illustrating the operation of the multiplex fluorescence detection device 10. Initially, a user specifies program parameters on the data acquisition device 21 or via an interface with control unit 23 (148). For example, these parameters may include a velocity and time period for rotating disk 13, define temperature profiles for the reaction, and sample locations on disk 13.

Next, the user loads disk 13 into the detection device 10 (150). Upon securing the device 10, the user starts the program (152), causing control unit 23 to begin spinning the disk (154) at the specified rate. After the disk has begun to spin, two concurrent processes may occur.

First, the detection device 10 starts to detect fluorescence from the excitation light (156) produced by one or more reactions within one or more samples. The detector 18 amplifies the fluorescence signals from each sample, which are synchronized to each respective sample and time at which the fluorescence was emitted (158). During this process, processor 122 saves the captured data to memory 124 and may communicate the data to data acquisition device 10 in real-time to monitor the progress of the run and for additional processing (160). Alternatively, processor 122 may save the data within device 10 until the program is complete. The processor 122 continues to detect florescence of the samples and save data until the program is complete (162). Once the run is complete, control unit 23 stops the disk from spinning (164).

During this process, control unit 23 monitors the disk temperature (166) and modulates the disk, or each sample, temperature to attain the target temperature for that time (168). The control unit 23 continues to monitor and control the temperatures until the program is complete (170). Once the run is complete, control unit 23 holds the temperature of the samples to a target storage temperature, usually 4 degrees Celsius (172).

The operation of device 10 may vary from the example of FIG. 12. For example, the disk revolutions per minute may be modified throughout the program, and laser 136 may be utilized to open valves between chambers on the disk to allow for multiple reactions. These steps may occur in any order within the operation, depending on the program the user defines.

Figure 13:
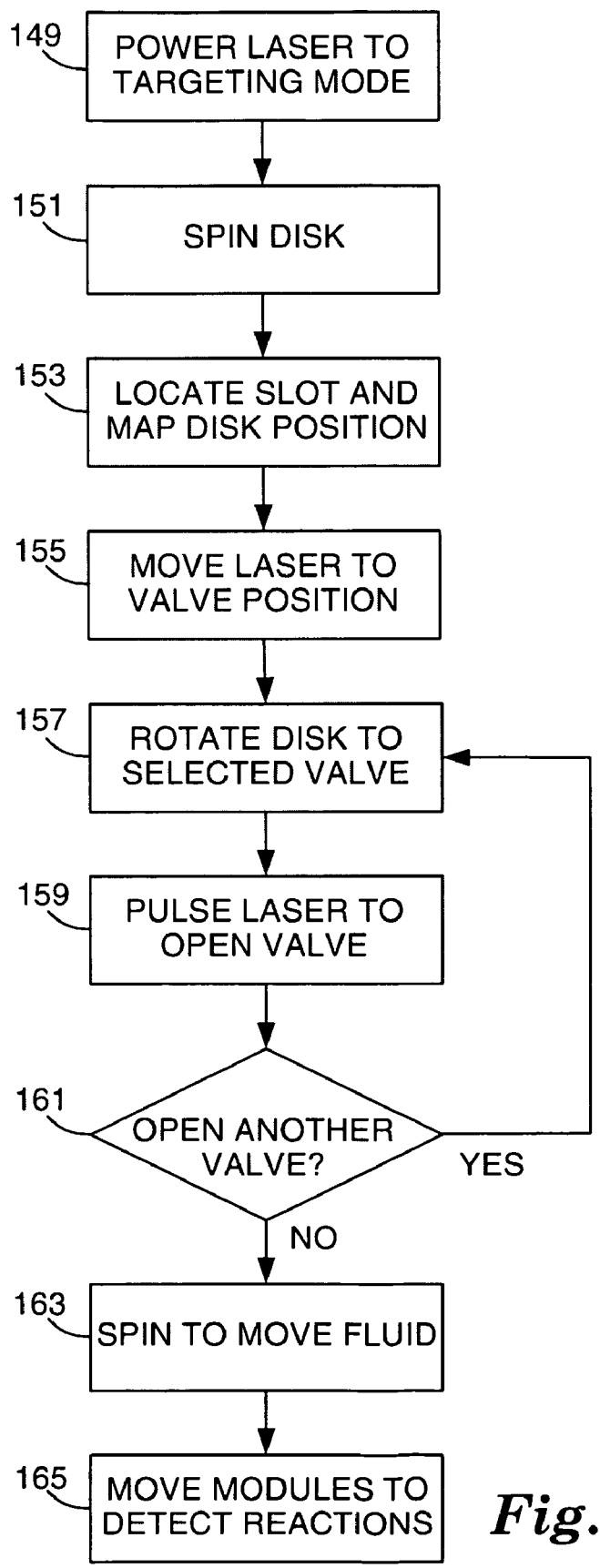
FIG. 13 is a flow diagram illustrating exemplary operation of the laser valve control system for the detection device.

FIG. 13 is a flow diagram illustrating exemplary operation of laser valve control system 51 of detection device 10. For exemplary purposes, FIG. 13 will be described in reference to disk 13A of FIG. 9A.

Initially, control unit 23 places laser valve control system 51 in a low-power mode (also referred to as a "targeting mode") that utilizes a reduced current (149). Next, control unit 23 initiates the rotation of disk 13A (151). NIR sensor 73 outputs a trigger signal to control unit 23 upon detecting the edges of slot 131 as disk 13A rotates, allowing control unit to accurately map the orientation of disk 13A and the locations of the valves on the disk to the known position of rotating platform 25 of device 10 (153).

Using the mapping, control unit 23 engages the gantry 60 to move laser valve control system 51 to the known location of the valves 127 relative to center hole 121 (155). Control unit 23 then rotates disk 13A to the first selected valve 127 to be opened (157). Next, control unit 23 places laser valve control system 51 in high-power mode and directs the system to produce a pulse of high energy laser light 71 to open the valve (159). If an additional valve need be opened (161) control unit 23 rotates disk 13A to the next valve (157) and opens the valve (159). If all valves have been opened, control unit 23 spins the disk 13A to move fluid, e.g., from holding chamber 125, through the open valve 127, and into process chamber 129 (163). In other embodiments, control unit 23 may continuously spin disk 13A while directing laser valve control system 51 to open valves.

Finally, control unit 23 engages the gantry 60 to move the optical modules to a radial position over the process chambers and commences detection of fluorescence from the reactions in the process chambers (165). In some embodiments, the contents of holding chambers 125 may act to deactivate or stabilize the products in process chambers 129. In this case, the detection device 10 may not need to monitor the new samples.

Figure 14A:
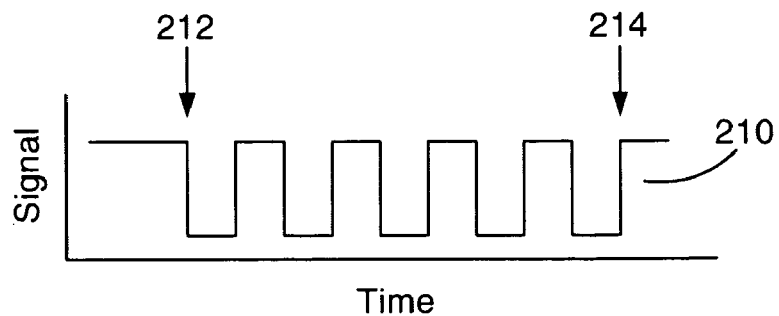
FIG. 14A is a timing diagram illustrating an exemplary method for detecting the inner and outer edges of a slot in a disk.
Figure 14B:
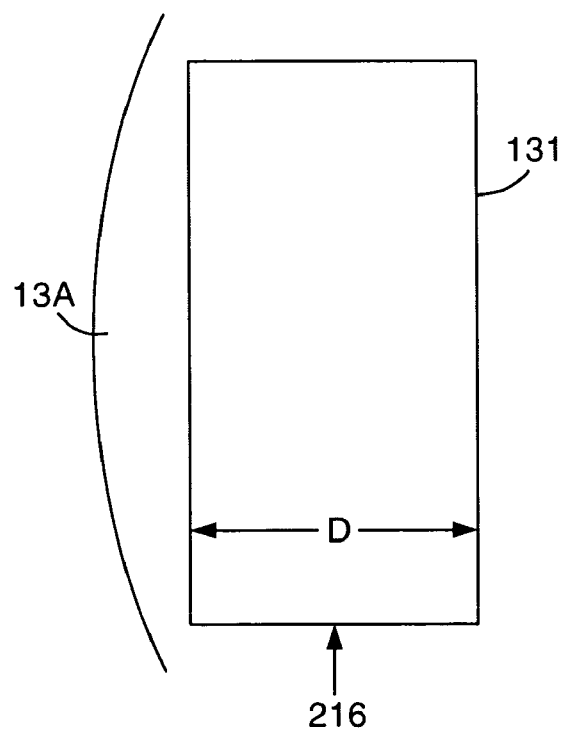
FIG. 14B is an exemplary diagram of a slot in a disk.
Figure 14C:
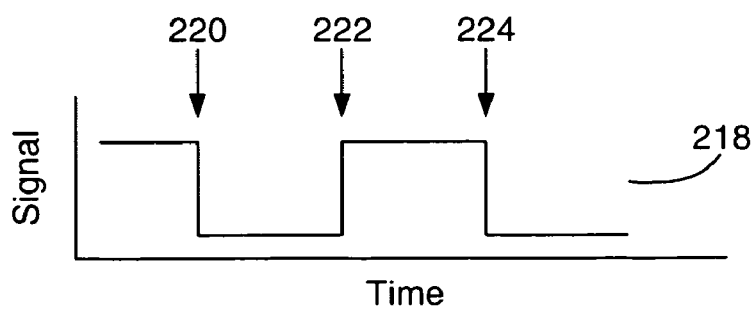
FIG. 14C is a timing diagram illustrating an exemplary method for determining the home position of a laser valve control system.

FIG. 14A is an exemplary diagram of a slot in a disk. In FIGS. 14A, 14B and 14C, disk 13A will be used as an exemplary disk in device 10. Disk 13A contains slot 131. Slot 131 includes outer edge 210, inner edge 214, leading edge 212 and trailing edge 216. Laser valve control system 51 detects each edge to provide an accurate map of disk 13A position. Distance D is the inner edge radial position subtracted from the outer edge radial position of slot 131. Each edge 210, 212, 214 and 216 create the detectable boundary between disk 13A material and the void in the disk described as slot 131. In some embodiments, slot 131 may be of any shape or size.

FIG. 14B is a timing diagram illustrating an exemplary method for detecting the inner and outer edges of a slot in a disk. Control unit 23 moves laser valve control system 51 away from disk 13. Disk 13A is spun while the gantry 60 moves laser valve control system towards the center of disk 13A.

Sensor 73 detects laser light 71 (FIG. 8) only when slot 131 allows laser light 71 to pass through disk 13A. A signal 218 from sensor 73 changes at spike 220 as outer edge 210 of slot 131 is detected while the gantry 60 is advancing inward. Signal 218 continues to modulate as slot 131 intermittently passes through laser light 71. Spike 222 indicates the last signal change which control unit 23 marks as inner edge 214 of slot 131. Control unit 23 now has a radial component of the map of disk 13 position. Control unit 23 moves laser valve control system 51 to the radial position halfway between the inner and outer edge radial positions. This position would be the radial position of inner edge 214 plus half of distance D. Positioning laser valve control system 51 to this location of slot 131 allows the system to detect the angular position of slot 131 without roundness of a corner of slot 131, e.g. the corner between inner edge 214 and trailing edge 216, causing error in the angular position of an edge of the slot. In some embodiments, disk 13A may not need to be rotated for laser valve control system 51 to detect the inner and outer edges of slot 131.

FIG. 14C is a timing diagram illustrating an exemplary method for determining the home position of a laser valve control system. Signal 224 is delivered to control unit 23 which indicates the presence of laser light 71. Laser valve control system 51 locates leading edge 212 and trailing edge 216 of slot 131 on disk 13A.

Signal 224 is constant as disk 13A is stationary. Once disk 13A is slowly rotated clock-wise, Spike 226 indicates the angular position of leading edge 212 of slot 131. Laser light 71 is detected by sensor 73 until trailing edge 216 is detected as spike 228. Control unit 23 stops disk 13A and slowly rotates disk 13A counter-clockwise until spike 230 indicates the presence of trailing edge 216 once more. Control unit 23 stores this angular position as the home angular position. Laser valve control system 51 now uses the radial position from FIG. 14A and angular position from FIG. 14C to locate valves or other structures on disk 13A. In other embodiments, laser valve control system 51 may only detect leading edge 212 or trailing edge 216 for effective positioning of disk 13A.

In some embodiments, disk 13A may be rotated in the opposite direction. In other embodiments, the exemplary signals from FIGS. 14B and 14C may be inverted and in any proportion relating the signal intensity to time. In other embodiments, laser valve control system 51 may first detect the angular position of disk 13A before detecting the radial position of disk 13A. The order of the described positioning method may be changed to accommodate certain applications, disks or technician preference.

Figure 15:
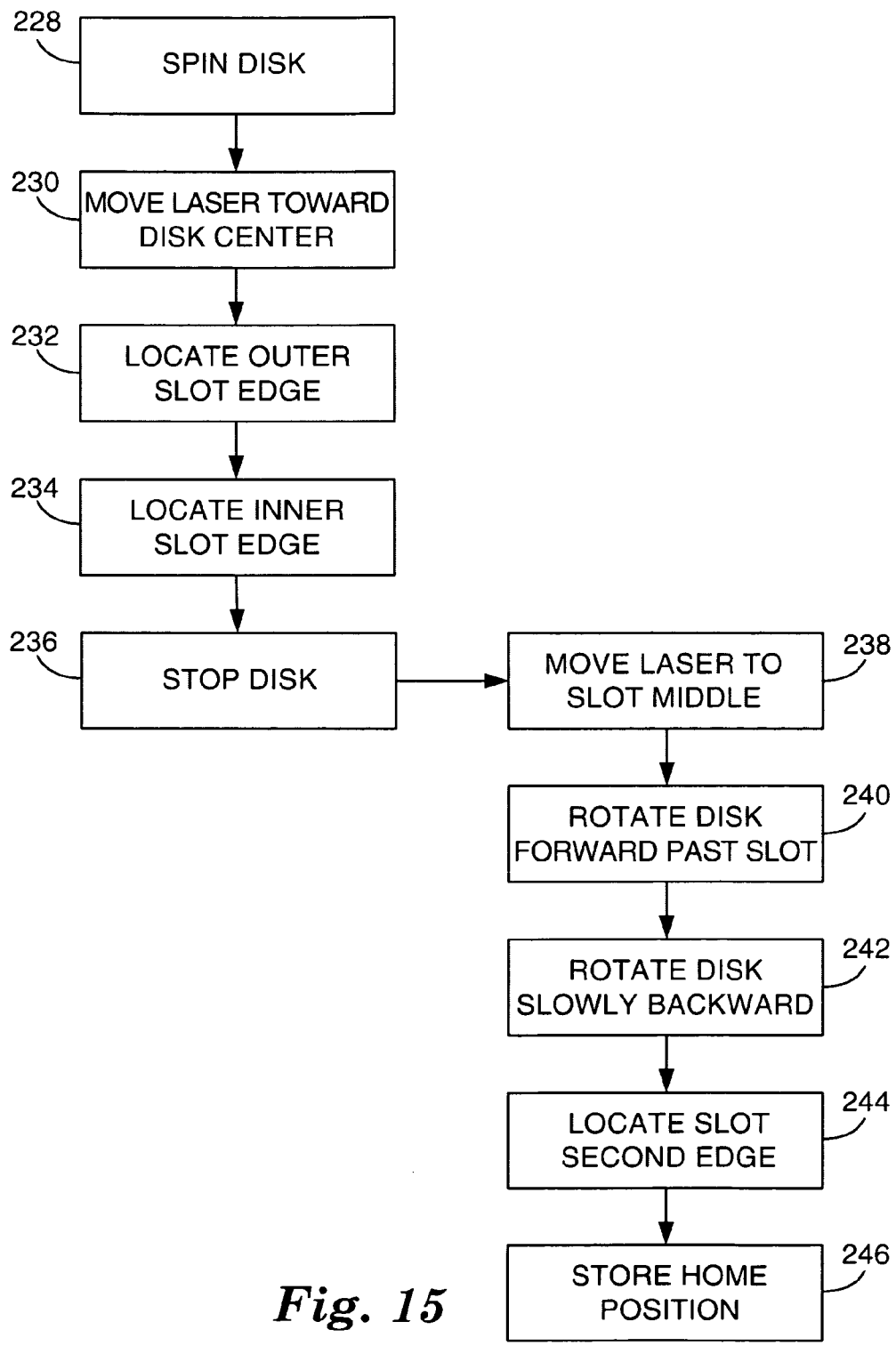
FIG. 15 is a flow diagram illustrating exemplary determination of the home position of a laser valve control system.

FIG. 15 is a flow diagram illustrating exemplary determination of the home position of a laser valve control system. Control unit 23 begins by spinning disk 13 (232). From outside of disk 13, the gantry 60 moves laser valve control system 51 toward the center of disk 13 (234). Laser valve control system 51 locates outer edge 210 of slot 131 in disk 13 and saves that outer radial position (236). As the gantry 60 continues to move, laser valve control system 51 locates inner edge 214 of slot 131 when laser light 71 in no longer detected by sensor 73 and saves that inner radial position (238). Control unit 23 stores the two radial positions and stops the rotation of disk 13 (240).

Control unit 23 moves laser valve control system 51 to the radial position directly in the middle between the inner and outer radial positions (242). Control unit 23 slowly rotates disk 13 to move both leading edge 212 and trailing edge 216 of slot 131 past laser valve control system 51 (244). Once trailing edge 216 is detected, the control unit slowly rotates disk 13 in the opposite direction (246). Upon detection of trailing edge 216 of slot 13 again, control unit 23 saves the location of the trailing edge (248) as the zero angular position or home angular position. Control unit 23 now has radial and angular positions of slot 131 and stores this information as the home position of disk 13 (250).

In some cases, slot sensor trigger 27 may work together with laser valve control system 51 to accurately map disk 13 position. For example, slot sensor trigger 27 may provide high resolution temporal position information while laser valve control system 51 provides high resolution spatial position information. Since both systems use the same structure of disk 13, cooperative positioning may provide more accurate positioning information.

EXAMPLE

Figure 16:
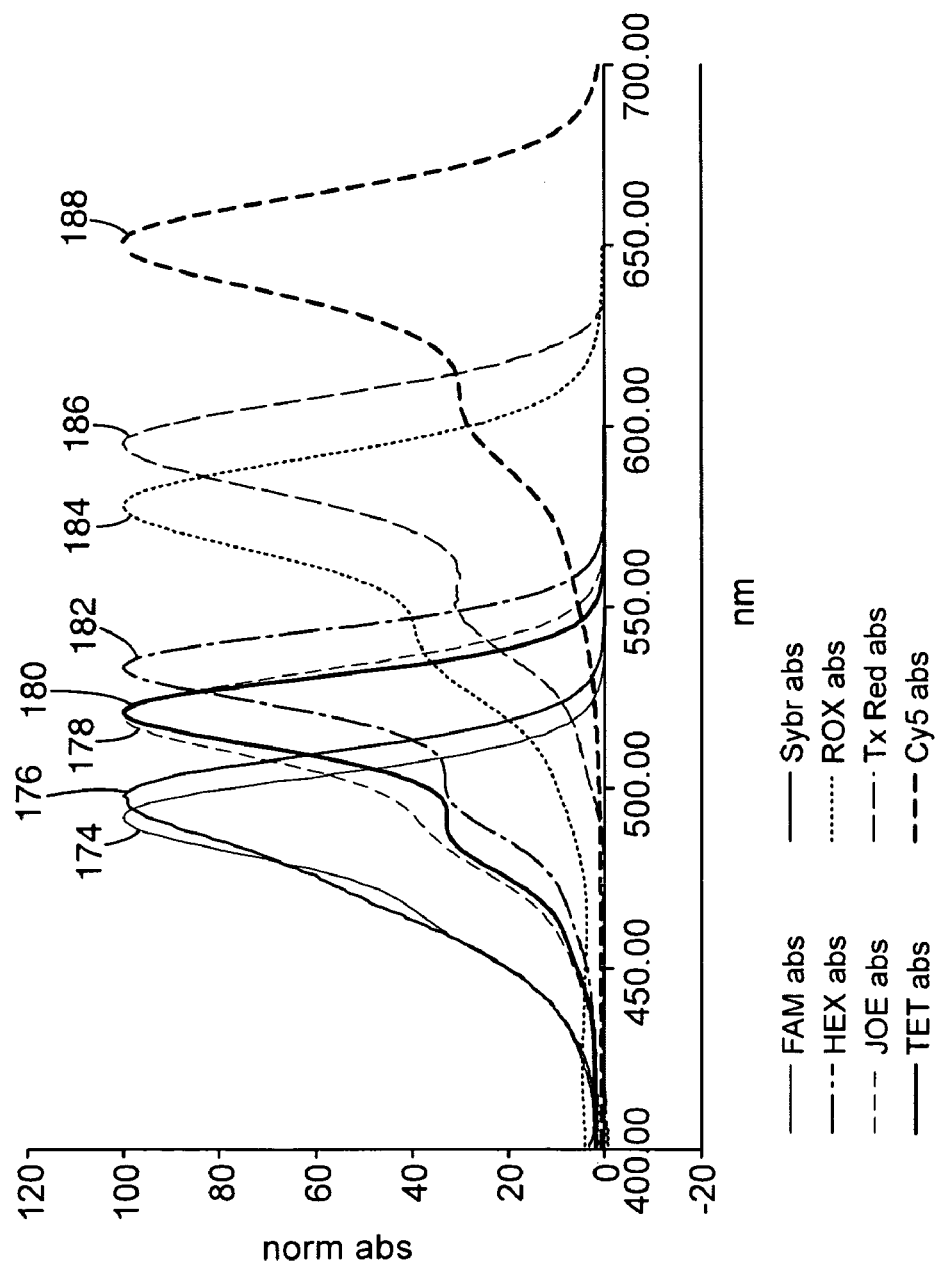
FIGS. 16 and 17 show the absorption and emission spectra of commonly used fluorescent dyes that may be utilized for multiplex PCR.
Figure 17:
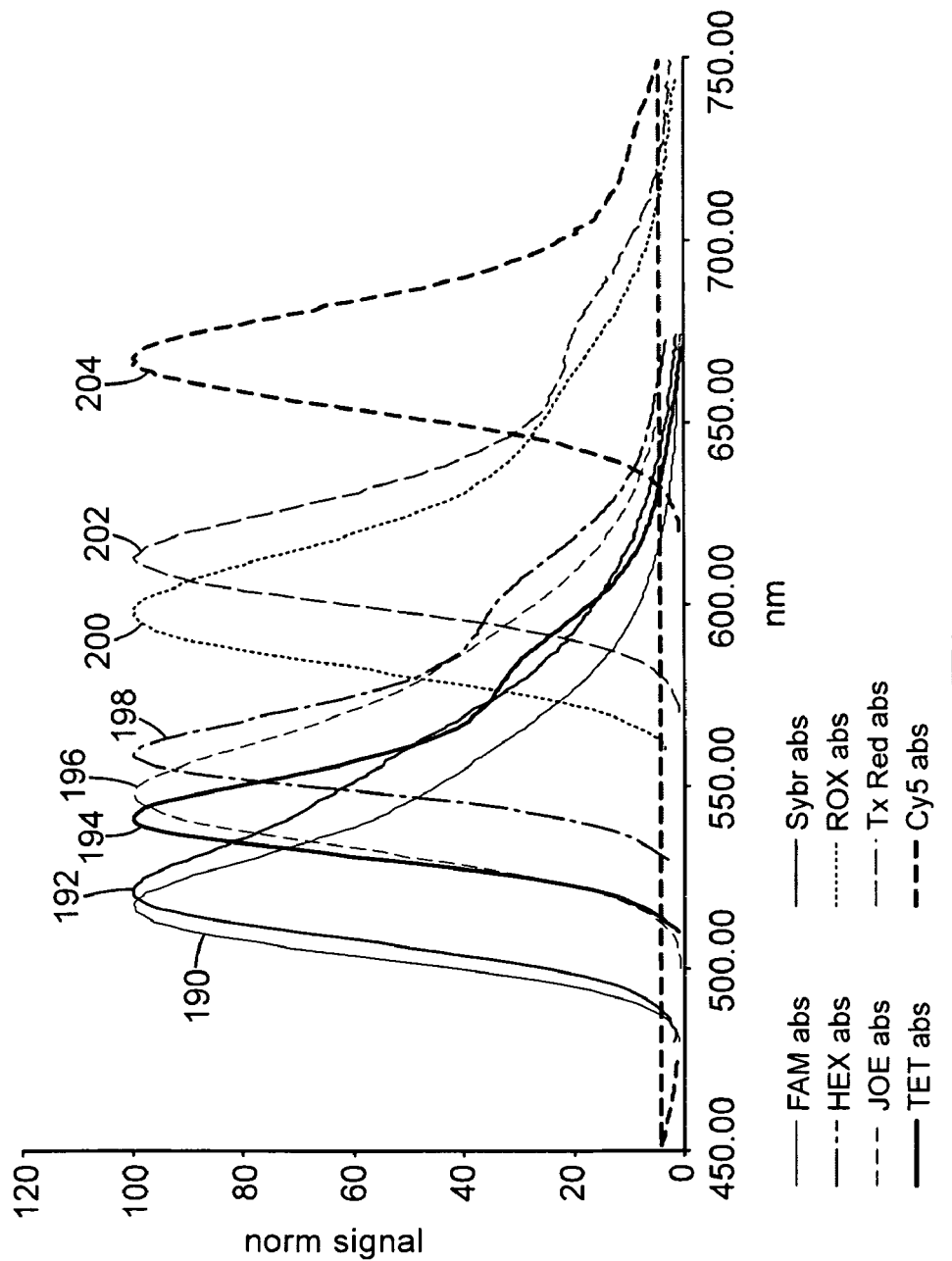

FIGS. 16 and 17 show the absorption and emission spectra of commonly used fluorescent dyes that may be utilized with device 10 for multiplex PCR. In these examples, the absorption maxima of the dyes vary from 480-620 nm, and the resulting emission maxima vary from 520-670 nm. The signals for each dye in FIG. 16 are numbered as FAM 174, Sybr 176, JOE 178, TET 180, HEX 182, ROX 184, Tx Red 186, and Cy5 188. The signals in FIG. 17 are FAM 190, Sybr 192, TET 194, JOE 196, HEX 198, ROX 200, Tx Red 202, and Cy5 204. FAM, HEX, JOE, VIC, TET, ROX are trademarks of Applera, Norwalk, Calif. Tamra is a trademark of AnaSpec, San Jose, Calif. Texas Red is a trademark of Molecular Probes. Cy 5 is a trademark of Amersham, Buckinghamshire, United Kingdom.

In one example, a 96 chamber disk was filled with different concentrations of FAM and ROX dye diluted in standard PCR reaction buffer. Four replicates of each dye were added in a 2× dilution series, starting from 200 nM FAM and 2000 nM ROX. Each sample volume was 10 μL. Chamber 82 had a mixture of 5 μL of 200 nM FAM and 5 μL of 2000 nM ROX. Device 10 was constructed as a two-channel multiplex PCR detection device having two optical modules 16 for detection of the dyes.

The first optical module (the FAM module) contained a blue LED, 475 nm excitation filter and a 520 nm detection filter. The second optical module (the ROX module) contained a green LED with a 560 nm excitation filter and a 610 nm detection filter. Another option would be to incorporate an orange LED and an excitation filter at 580 nm to optimize for ROX detection.

A PCR analysis was conducted, and fluorescent signals from the samples were multiplexed into a bifurcated fiber optic bundle. The fiber bundle was interfaced with a single detector, specifically a photomultiplier tube (PMT). Data was collected by a National Instruments data acquisition (DAQ) board interfaced with a Visual Basic data acquisition program executing on a general-purpose computer. Data was acquired while the disk was spinning at 1000 revolutions per minute (nominally). The FAM module and the ROX module were sequentially used to interrogate the samples. Each scan consisted of an average of 50 rotations. The raw data from the two optical modules is shown in FIGS. 18A and 18B.

Figure 18A:
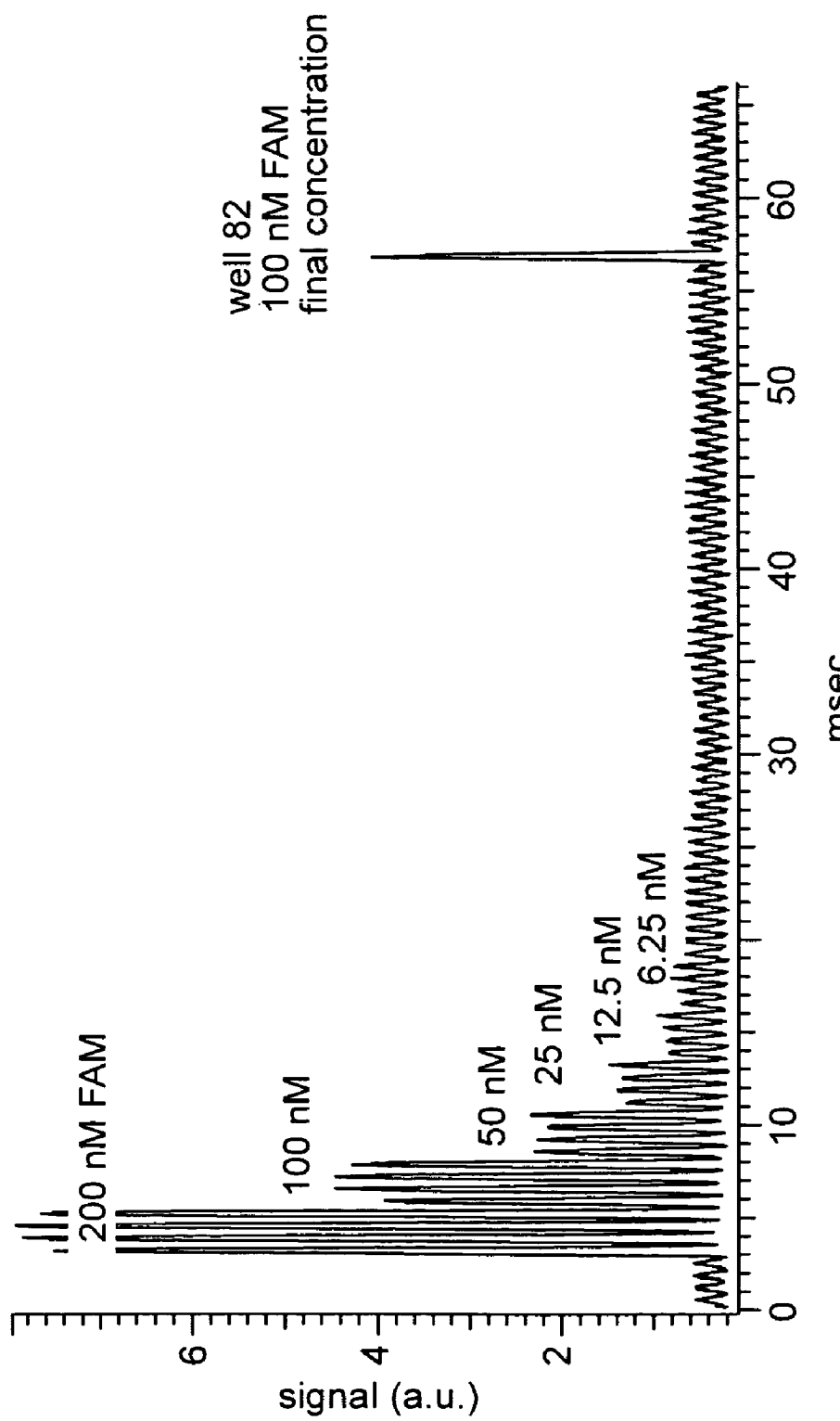
FIGS. 18A and 18B illustrate raw data acquired from two exemplary detection modules with a single detector during a PCR analysis.
Figure 18B:
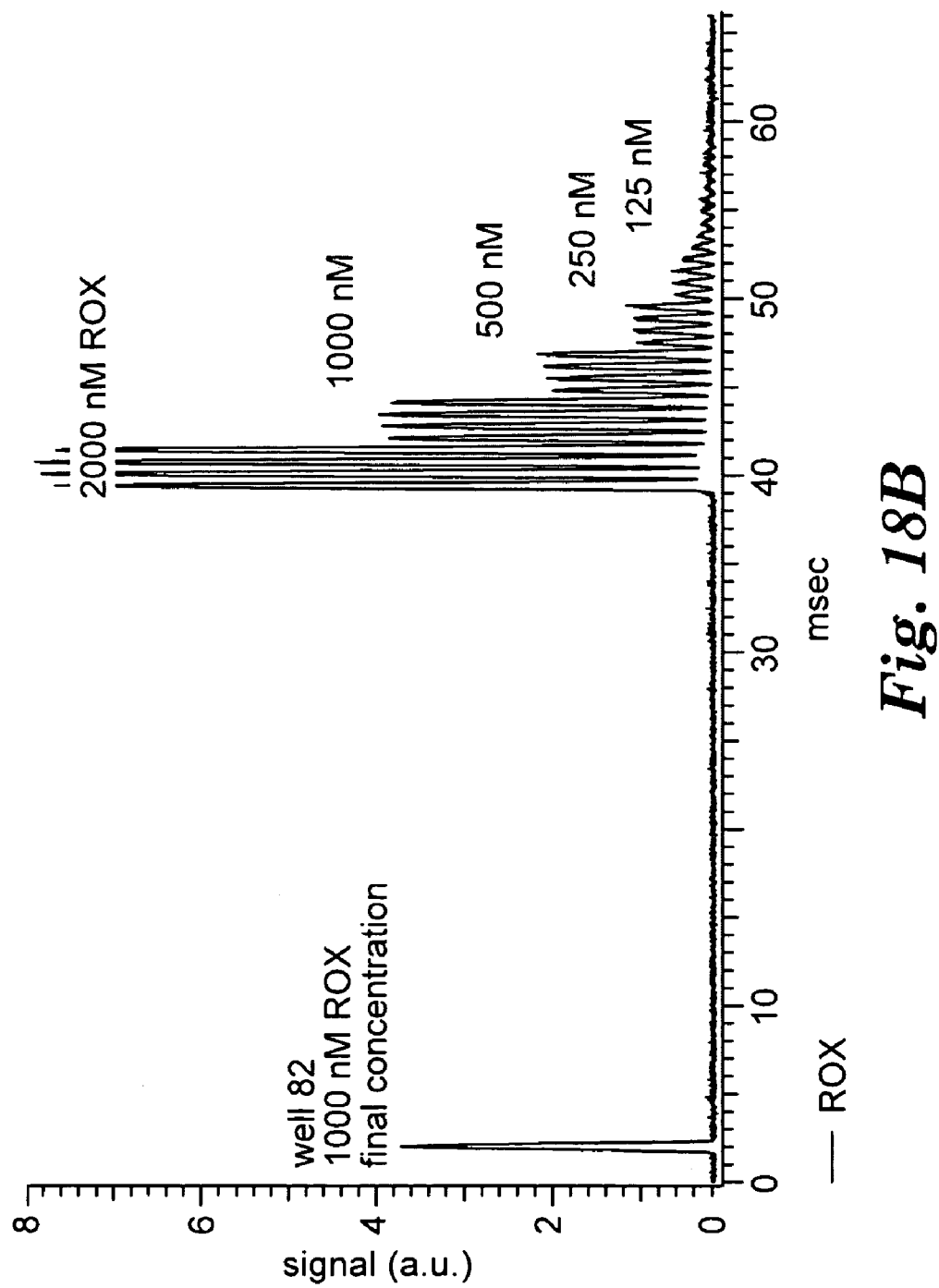

The graph in FIG. 18A was acquired by powering the LED in the FAM module, and the graph in FIG. 18B was acquired by powering the LED in the ROX module.

During the analysis, the collected data clearly showed that there was a time offset associated with optical modules being physically located over different chambers at any one time. An offset value was calculated by determining the time offset between optical modules 1 and 2 for a particular chamber, i.e., chamber 82 in this case. In other words, the time offset indicates the amount of time delay between data captured by the FAM module and data captured by the ROX module for the same chamber.

Figure 19:
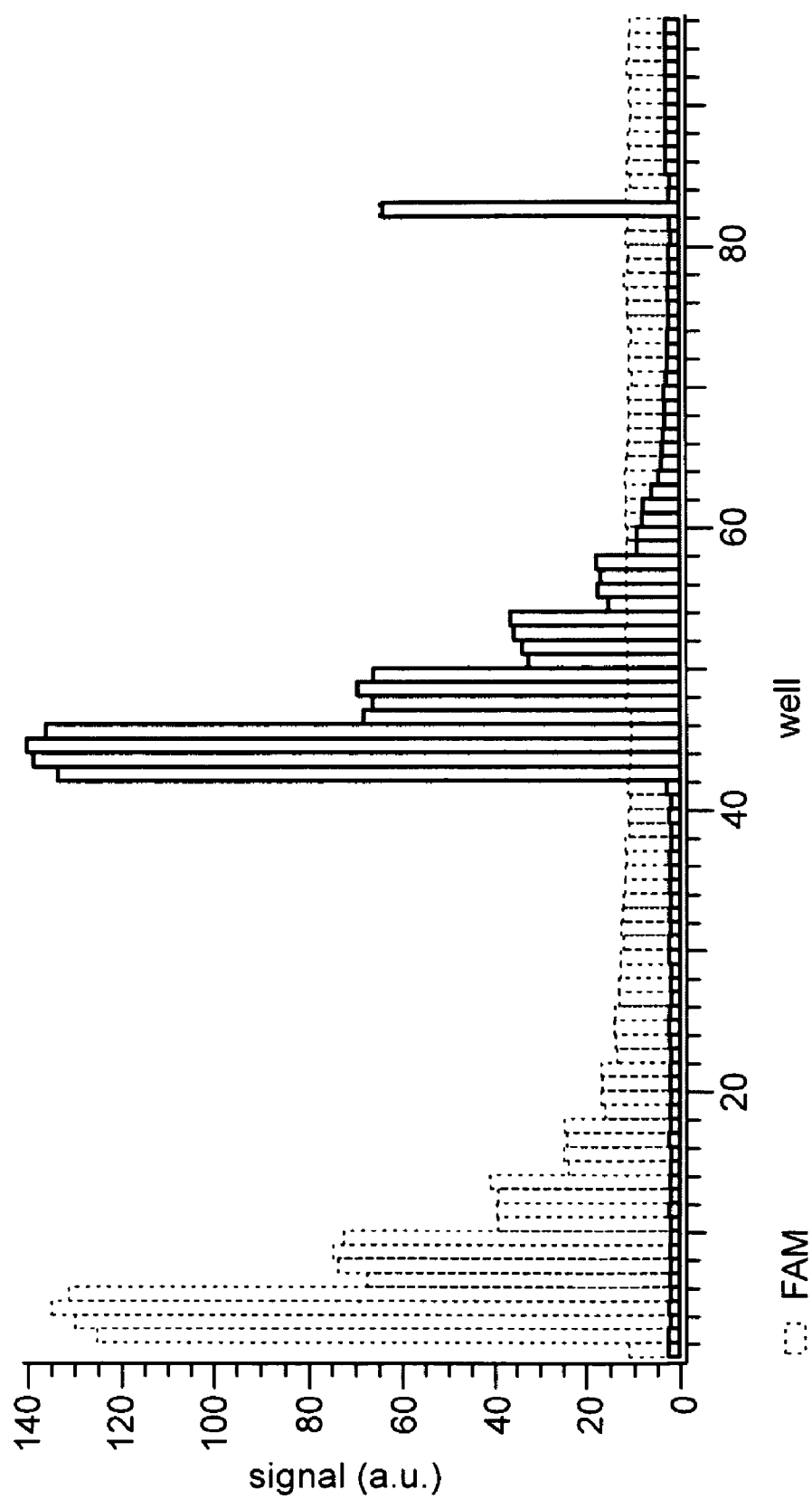
FIG. 19 is a graph that shows the data once adjusted for a time offset.

FIG. 19 is a graph that shows the offset-subtracted integrated data for each chamber. FAM is indicated by dotted line bars, ROX is indicated by solid line bars, and the ROX data is placed over the FAM data. The data showed that there was no signal from the ROX dye on optical module 1 and no signal from the FAM dye on optical module 2. There was a higher background on optical module 1, which may be rectified by using an optimized set of filters. The data was analyzed to determine the limit of detection (LOD), described as the signal equivalent to the baseline noise level. The baseline noise level was defined as the average of ten scans of a blank chamber plus 3 times the standard deviation.

Figure 20A:
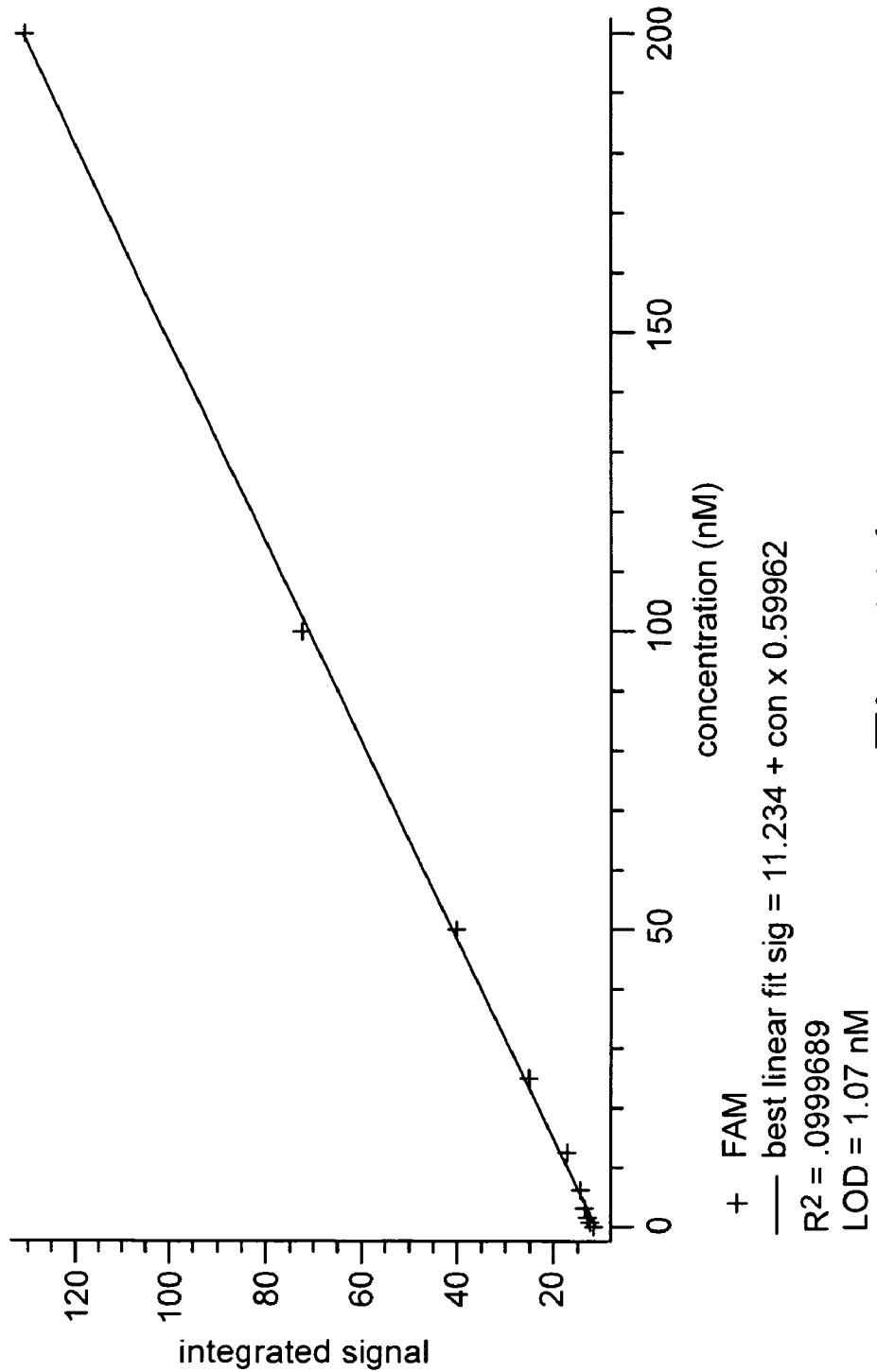
FIGS. 20A and 20B show a limit of detection (LOD) for the data received from two exemplary detection modules.
Figure 20B:
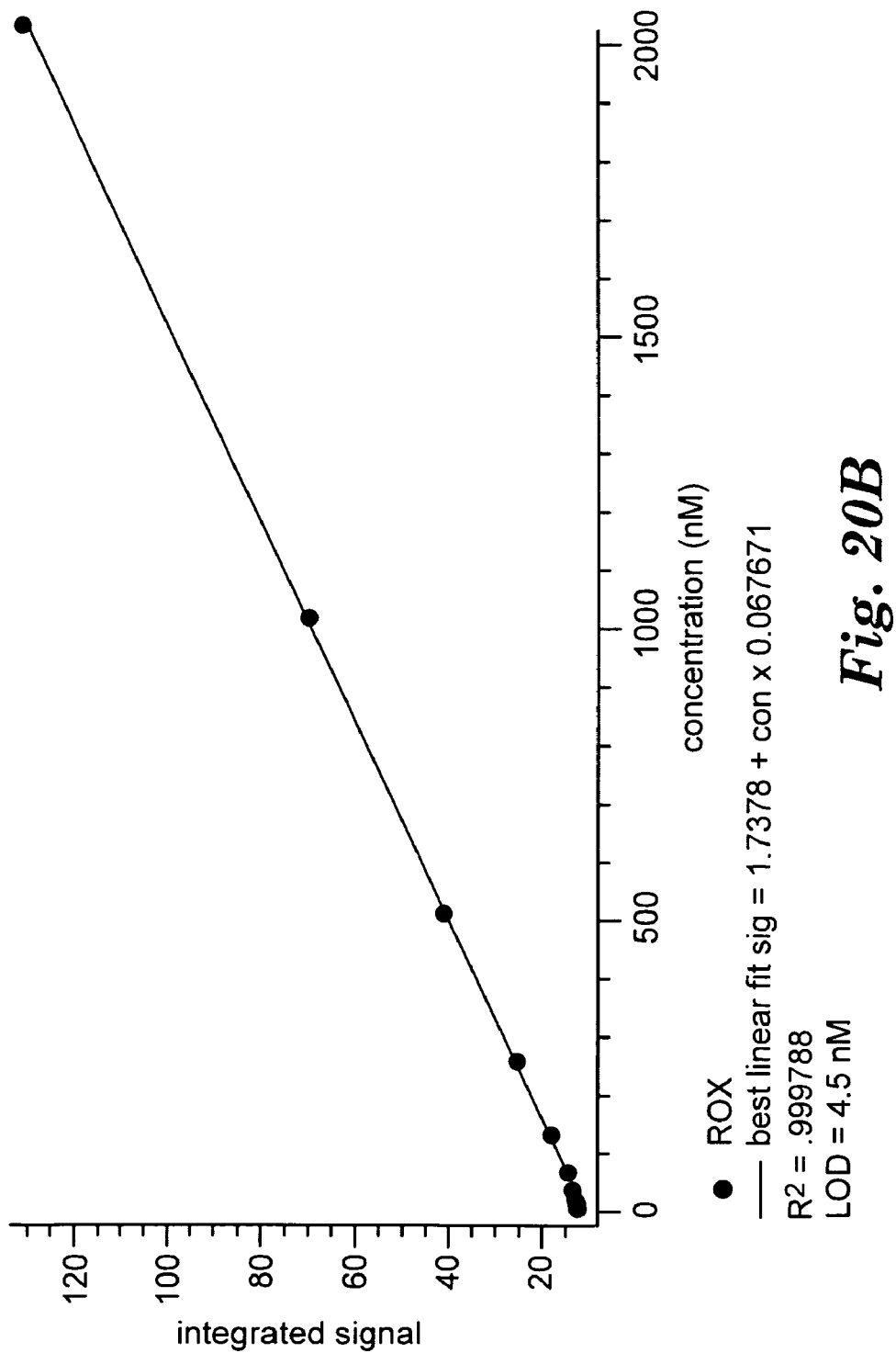

The LOD was determined by a linear least squares fit of the integrated signal plotted against the concentration of the FAM and ROX standards. The LOD of the FAM and ROX modules were calculated to be 1 and 4 nM, respectively, as shown in FIGS. 20A and 20B.

Various embodiments of the invention have been described. These and other embodiments are within the scope of the following claims.

The invention claimed is:

1. A method for controlling a valve on a disk, the method comprising the steps of:
    providing the disk having a holding chamber and a process chamber, the holding chamber separated from the process chamber by the valve;
    providing a motor configured to rotate the disk;
    providing a laser control system comprising a sensor coupled to a controller and a single laser that emits electromagnetic energy at a first level to determine the position of a structure of the disk and emits electromagnetic energy at second energy level to open the valve to permit fluid to flow from the holding chamber to the process chamber, wherein the first energy level is different from the second energy level; and
    detecting the electromagnetic energy at the first level with the sensor and outputting a signal;
    wherein in response to the signal from the sensor the control unit performs the following steps:
    constructs a position map based on the signal that maps a position of the valve relative to a known position of the motor,
    uses the position map to rotate the disk and move the laser to target the valve, and
    instructs the laser to output electromagnetic energy at the second energy level to open the valve to permit fluid to flow from the holding chamber to the process chamber.

2. The method of claim 1, wherein the structure is a slot that allows the electromagnetic energy to pass the electromagnetic energy from the laser to the sensor.

3. The method of claim 2, wherein the sensor detects the electromagnetic energy from the laser when the slot in the disk is aligned between the energy source and the sensor.

4. The method of claim 2, wherein the slot in the disk is the shape of a rectangle, circle, oval, ellipse or an irregular shape.

5. The method of claim 2, further comprising detecting the edges of the slot for determining the precise location of the valve on the disk.

6. The method of claim 1, further comprising selecting the valve for opening based on one or more reactions specified by a user, and targeting the electromagnetic energy to the selected valve on the disk based upon the map.

7. The method of claim 6, further comprising producing a pulse of electromagnetic energy to heat and open the valve to allow fluid communication between the holding chamber and the process chamber.

8. The method of claim 1, further comprising aligning the laser to a precise location on the disk with a gantry.

9. The method of claim 8, further comprising aligning a plurality of optical modules to one or more process chambers with the gantry.

10. The method of claim 9, further comprising:
    exciting the disk with a plurality of light beams from the plurality of optical modules to produce a plurality of emitted fluorescent light beams; and
    capturing the fluorescent light beams with the plurality of optical modules;
    wherein the optical modules are optically configured for the different wavelengths.

11. The method of claim 10, wherein the laser is included in one of the plurality of optical modules.

12. The method of claim 1, wherein the laser produces low-energy near-infrared light for determining the position of the disk and high-energy near-infrared light for opening the valve.

13. The method of claim 1, wherein the process chamber holds a sample and a plurality of fluorescent dyes.

14. The method of claim 1, wherein the structure is a slot formed by the disk or a tab.

15. The method of claim 1, wherein the first level of electromagnetic energy is low energy near-infrared light.

16. The method of claim 1, wherein the second level of electromagnetic energy is laser or high-energy near-infrared light.

17. The method of claim 1, further comprising: wherein detecting the position of the structure of the disk includes:

emitting electromagnetic energy at the first level while rotating the disk to determine a radial position of a structure of the disk; and emitting electromagnetic energy at the first level while rotating the disk to determine an angular position of the structure of the disk; and wherein emitting electromagnetic energy at the second level to open the valve to permit fluid to flow from the holding chamber to the process chamber includes using the radial position and the angular position to direct electromagnetic energy to the valve to enable fluid communication between the holding chamber and the process chamber.

18. The method of claim 1, wherein emitting electromagnetic energy at the second level to open the valve includes producing a pulse of electromagnetic energy to heat and open the valve.

* * * * *

UNITED STATES PATENT AND TRADEMARK OFFICE
CERTIFICATE OF CORRECTION

PATENT NO. : 7,867,767 B2
APPLICATION NO. : 12/419008
DATED : January 11, 2011
INVENTOR(S) : William Bedingham et al.

It is certified that error appears in the above-identified patent and that said Letters Patent is hereby corrected as shown below:

Column 3
Line 29, After "7" insert -- is --.
Line 42, Delete "the a" and insert -- a --, therefor.

Column 23
Line 1, Delete "(151 )." and insert -- (151). --, therefor.

Column 26
Lines 34-35, In Claim 2, after "pass" delete "the electromagnetic energy".

Column 27
Line 14, In Claim 17, after "claim 1," delete "further comprising:".

Signed and Sealed this
Twenty-second Day of March, 2011

David J. Kappos
*Director of the United States Patent and Trademark Office*